(12) United States Patent
Siegel et al.

(10) Patent No.: US 12,370,043 B2
(45) Date of Patent: Jul. 29, 2025

(54) DEVICE FOR SECURING HEART VALVE LEAFLETS

(71) Applicant: CEDARS-SINAI MEDICAL CENTER, Los Angeles, CA (US)

(72) Inventors: Robert James Siegel, Beverly Hills, CA (US); Lawrence Eric Ong, Beverly Hills, CA (US); Werner Hafelfinger, Thousand Oaks, CA (US); Niclas Henning Zieger, Pasadena, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 17/649,716

(22) Filed: Feb. 2, 2022

(65) Prior Publication Data

US 2022/0226113 A1    Jul. 21, 2022

Related U.S. Application Data

(62) Division of application No. 15/746,788, filed as application No. PCT/US2016/043750 on Jul. 22, 2016, now Pat. No. 11,241,308.

(60) Provisional application No. 62/196,276, filed on Jul. 23, 2015.

(51) Int. Cl.
*A61F 2/24* (2006.01)
*A61B 17/00* (2006.01)

(52) U.S. Cl.
CPC ............ *A61F 2/2427* (2013.01); *A61F 2/246* (2013.01); *A61F 2/2466* (2013.01); *A61B 2017/00243* (2013.01); *A61B 2017/00477* (2013.01)

(58) Field of Classification Search
CPC ..... A61B 17/08; A61B 17/122; A61B 17/128; A61B 17/1285; A61B 2017/00477; A61B 2017/0057; A61B 2017/00579; A61B 2017/00584; A61B 2017/00606; A61B 2017/00619; A61B 2017/00623; A61B 2017/00643; A61F 2/246; A61F 2/2466
See application file for complete search history.

(56) References Cited

U.S. PATENT DOCUMENTS

| 4,777,951 | A |   | 10/1988 | Cribier |
| 5,171,259 | A | * | 12/1992 | Inoue ................. A61B 17/0057 606/232 |
| 5,201,880 | A |   | 4/1993  | Wright et al. |

(Continued)

FOREIGN PATENT DOCUMENTS

| CN | 106175986 | 12/2016 |
| EP | 1 674 040 | 6/2006  |

(Continued)

OTHER PUBLICATIONS

Bhargava et al., "Biosense Left Ventricular Electromechanical Mapping", Asian Cardiovasc Thorac Ann 1999, 7:345-52.

(Continued)

*Primary Examiner* — Sarah W Aleman
(74) *Attorney, Agent, or Firm* — Knobbe, Martens, Olson & Bear, LLP

(57) ABSTRACT

A fixation device for securing together leaflets of a heart valve is provided. The fixation device may comprise two plates that are disposed on either side of the tricuspid valve. The plates may be secured to one another by a locking clip, thereby securing the valve leaflets between the plates.

14 Claims, 28 Drawing Sheets

(56) References Cited

U.S. PATENT DOCUMENTS

| | | |
|---|---|---|
| 5,573,540 A | 11/1996 | Yoon |
| 5,575,799 A | 11/1996 | Bolanos et al. |
| 5,609,598 A | 3/1997 | Laufer et al. |
| 5,626,588 A | 5/1997 | Sauer et al. |
| 5,716,367 A | 2/1998 | Koike et al. |
| 6,029,671 A | 2/2000 | Stevens et al. |
| 6,051,014 A | 4/2000 | Jang |
| 6,090,096 A | 7/2000 | St. Goar et al. |
| 6,117,144 A | 9/2000 | Nobles et al. |
| 6,117,145 A | 9/2000 | Wood et al. |
| 6,136,010 A | 10/2000 | Modesitt et al. |
| 6,165,183 A | 12/2000 | Kuehn et al. |
| 6,197,043 B1 | 3/2001 | Davidson |
| 6,206,893 B1 | 3/2001 | Klein et al. |
| 6,269,819 B1 | 8/2001 | Oz et al. |
| 6,287,321 B1 | 9/2001 | Jang |
| 6,312,446 B1 | 11/2001 | Huebsch et al. |
| 6,312,447 B1 | 11/2001 | Grimes |
| 6,325,067 B1 | 12/2001 | Sterman et al. |
| 6,328,757 B1 | 12/2001 | Matheny |
| 6,461,366 B1 | 10/2002 | Seguin |
| 6,508,828 B1 | 1/2003 | Akerfeldt et al. |
| 6,575,971 B2 | 6/2003 | Hauck et al. |
| 6,629,534 B1 | 10/2003 | Goar et al. |
| 6,635,068 B1 | 10/2003 | Dubrul et al. |
| 6,752,813 B2 | 6/2004 | Goldfarb et al. |
| 6,770,083 B2 | 8/2004 | Seguin |
| 6,926,715 B1 | 8/2005 | Hauck et al. |
| 6,932,792 B1 | 8/2005 | St. Goar et al. |
| 6,945,978 B1 | 9/2005 | Hyde |
| 7,048,754 B2 | 5/2006 | Martin et al. |
| 7,226,467 B2 | 6/2007 | Lucatero et al. |
| 7,276,078 B2 | 10/2007 | Spenser et al. |
| 7,404,824 B1 | 7/2008 | Webler et al. |
| 7,563,267 B2 | 7/2009 | Goldfarb et al. |
| 7,569,062 B1 * | 8/2009 | Kuehn ............... A61B 17/064 |
| | | 623/2.11 |
| 7,604,646 B2 | 10/2009 | Goldfarb et al. |
| 7,632,308 B2 | 12/2009 | Loulmet |
| 7,635,329 B2 | 12/2009 | Goldfarb et al. |
| 7,666,204 B2 | 2/2010 | Thornton et al. |
| 7,704,269 B2 | 4/2010 | St. Goar et al. |
| 7,736,388 B2 | 6/2010 | Goldfarb et al. |
| 7,811,296 B2 | 10/2010 | Goldfarb et al. |
| 7,828,819 B2 | 11/2010 | Webler et al. |
| 7,854,762 B2 | 12/2010 | Speziali et al. |
| 7,938,827 B2 | 5/2011 | Hauck et al. |
| 7,981,123 B2 | 7/2011 | Seguin |
| 8,052,592 B2 | 11/2011 | Goldfarb et al. |
| 8,123,703 B2 | 2/2012 | Martin et al. |
| 8,172,856 B2 | 5/2012 | Eigler et al. |
| 8,216,256 B2 | 7/2012 | Raschdorf, Jr. et al. |
| 8,216,302 B2 | 7/2012 | Wilson et al. |
| 8,303,608 B2 | 11/2012 | Goldfarb et al. |
| 8,323,334 B2 | 12/2012 | Deem et al. |
| 8,382,796 B2 | 2/2013 | Blaeser et al. |
| 8,409,219 B2 | 4/2013 | Kelley et al. |
| 8,409,273 B2 | 4/2013 | Thornton et al. |
| 8,545,551 B2 | 10/2013 | Loulmet |
| 8,568,472 B2 | 10/2013 | Marchand et al. |
| 8,920,463 B2 | 12/2014 | McGukin, Jr. et al. |
| 8,932,325 B2 | 1/2015 | Stanley et al. |
| 8,992,605 B2 | 3/2015 | Zakai et al. |
| 9,023,099 B2 | 5/2015 | Duffy et al. |
| 9,060,858 B2 | 6/2015 | Thornton et al. |
| 9,474,605 B2 | 10/2016 | Rowe et al. |
| 9,498,330 B2 | 11/2016 | Solem |
| 9,763,658 B2 | 9/2017 | Eigler et al. |
| 10,080,657 B2 | 9/2018 | Siegel |
| 10,105,221 B2 | 10/2018 | Siegel |
| 10,478,304 B2 | 11/2019 | McNiven et al. |
| 10,499,905 B2 | 12/2019 | Eigler et al. |
| 10,758,241 B1 | 9/2020 | Lashinski et al. |
| 10,758,265 B2 | 9/2020 | Siegel |
| 10,799,359 B2 | 10/2020 | Siegel et al. |
| 10,898,323 B2 | 1/2021 | Siegel |
| 11,241,308 B2 | 2/2022 | Siegel et al. |
| 11,291,544 B2 | 4/2022 | Siegel et al. |
| 11,439,501 B2 | 9/2022 | Siegel et al. |
| 11,653,948 B2 | 5/2023 | Siegel |
| 11,730,591 B2 | 8/2023 | Siegel et al. |
| 2001/0005787 A1 | 6/2001 | Oz et al. |
| 2002/0013571 A1 | 1/2002 | Goldfarb et al. |
| 2002/0183787 A1 * | 12/2002 | Wahr ................ A61B 18/1492 |
| | | 606/213 |
| 2003/0120340 A1 | 6/2003 | Liska et al. |
| 2004/0044350 A1 | 3/2004 | Martin et al. |
| 2004/0260322 A1 | 12/2004 | Rudko et al. |
| 2005/0033446 A1 | 2/2005 | Deem et al. |
| 2005/0107871 A1 | 5/2005 | Realyvasquez et al. |
| 2005/0143811 A1 | 6/2005 | Realyvasquez |
| 2005/0222489 A1 | 10/2005 | Rahdert et al. |
| 2005/0273135 A1 | 12/2005 | Chanduszko et al. |
| 2006/0004442 A1 | 1/2006 | Spenser et al. |
| 2006/0020275 A1 | 1/2006 | Goldfarb et al. |
| 2006/0074484 A1 | 4/2006 | Huber |
| 2006/0089671 A1 | 4/2006 | Goldfarb et al. |
| 2006/0229708 A1 | 10/2006 | Powell et al. |
| 2006/0241745 A1 | 10/2006 | Solem |
| 2006/0293739 A1 | 12/2006 | Vijay |
| 2007/0032850 A1 | 2/2007 | Ruiz et al. |
| 2007/0038293 A1 | 2/2007 | St.Goar et al. |
| 2007/0055303 A1 | 3/2007 | Vidlund et al. |
| 2007/0093890 A1 | 4/2007 | Eliasen et al. |
| 2007/0198082 A1 | 8/2007 | Kapadia et al. |
| 2007/0255273 A1 | 11/2007 | Fernandez et al. |
| 2007/0270943 A1 | 11/2007 | Solem et al. |
| 2007/0293943 A1 | 12/2007 | Quinn |
| 2009/0048668 A1 | 2/2009 | Wilson et al. |
| 2009/0062836 A1 | 3/2009 | Kurrus |
| 2009/0076600 A1 | 3/2009 | Quinn |
| 2009/0177266 A1 | 7/2009 | Powell et al. |
| 2010/0022823 A1 | 1/2010 | Goldfarb et al. |
| 2010/0217283 A1 | 8/2010 | St.Goar et al. |
| 2010/0298929 A1 | 11/2010 | Thornton et al. |
| 2011/0029071 A1 | 2/2011 | Zlotnick et al. |
| 2011/0066233 A1 | 3/2011 | Thornton et al. |
| 2011/0082495 A1 * | 4/2011 | Ruiz ................ A61B 17/0057 |
| | | 606/213 |
| 2011/0106245 A1 | 5/2011 | Miller et al. |
| 2011/0137397 A1 | 6/2011 | Chau et al. |
| 2011/0218620 A1 | 9/2011 | Meiri et al. |
| 2011/0224655 A1 | 9/2011 | Asirvatham et al. |
| 2011/0264208 A1 | 10/2011 | Duffy et al. |
| 2011/0313437 A1 | 12/2011 | Yeh |
| 2011/0319989 A1 | 12/2011 | Lane et al. |
| 2012/0010700 A1 | 1/2012 | Spenser |
| 2012/0065464 A1 | 3/2012 | Ellis et al. |
| 2012/0078360 A1 | 3/2012 | Rafiee |
| 2012/0095547 A1 | 4/2012 | Chuter |
| 2012/0116418 A1 | 5/2012 | Belson et al. |
| 2012/0191181 A1 | 7/2012 | Kassab et al. |
| 2012/0245678 A1 | 9/2012 | Solem |
| 2012/0310334 A1 | 12/2012 | Dolan |
| 2013/0018414 A1 | 1/2013 | Widimski et al. |
| 2013/0030522 A1 | 1/2013 | Rowe et al. |
| 2013/0066341 A1 * | 3/2013 | Ketai ..................... A61F 2/246 |
| | | 606/151 |
| 2013/0110227 A1 | 5/2013 | Quadri et al. |
| 2013/0197559 A1 | 8/2013 | Hariton et al. |
| 2013/0226288 A1 | 8/2013 | Goldwasser et al. |
| 2013/0253547 A1 | 9/2013 | Goldfarb et al. |
| 2013/0261739 A1 | 10/2013 | Kuehn |
| 2013/0297010 A1 | 11/2013 | Bishop et al. |
| 2013/0338764 A1 | 12/2013 | Thornton et al. |
| 2014/0039607 A1 | 2/2014 | Kovach |
| 2014/0039608 A1 * | 2/2014 | Eidenschink ......... A61F 2/2463 |
| | | 623/2.11 |
| 2014/0058502 A1 | 2/2014 | Marchand et al. |
| 2014/0222136 A1 | 8/2014 | Geist et al. |
| 2014/0236198 A1 | 8/2014 | Goldfarb et al. |
| 2014/0277426 A1 | 9/2014 | Dakin et al. |
| 2014/0371789 A1 | 12/2014 | Hariton et al. |
| 2015/0038988 A1 | 2/2015 | Tegels et al. |

(56) References Cited

U.S. PATENT DOCUMENTS

| | | |
|---|---|---|
| 2015/0134057 A1 | 5/2015 | Rourke et al. |
| 2015/0173765 A1 | 6/2015 | Miller et al. |
| 2016/0324635 A1 | 11/2016 | Vidlund et al. |
| 2017/0100250 A1 | 4/2017 | Marsot et al. |
| 2017/0143478 A1 | 5/2017 | Schwartz et al. |
| 2017/0174979 A1 | 6/2017 | Sanders |
| 2017/0216028 A1 | 8/2017 | Khalil |
| 2017/0325842 A1 | 11/2017 | Siegel et al. |
| 2018/0193016 A1 | 7/2018 | Eigler et al. |
| 2018/0289478 A1 | 10/2018 | Quill |
| 2019/0008638 A1 | 1/2019 | Siegel et al. |
| 2019/0343630 A1 | 11/2019 | Kizuka |
| 2019/0365529 A1 | 12/2019 | Siegel et al. |
| 2020/0030092 A1 | 1/2020 | Tuval et al. |
| 2020/0121454 A1 | 4/2020 | Spence |
| 2020/0367926 A1 | 11/2020 | Siegel |
| 2021/0030534 A1 | 2/2021 | Siegel et al. |
| 2023/0050824 A1 | 2/2023 | Siegel et al. |
| 2024/0277468 A1 | 8/2024 | Siegel et al. |

FOREIGN PATENT DOCUMENTS

| | | |
|---|---|---|
| EP | 1 539 015 | 4/2011 |
| EP | 3 269 330 | 1/2018 |
| JP | H05-220174 | 8/1993 |
| JP | 2004-008805 | 1/2004 |
| JP | 2004-530451 | 10/2004 |
| JP | 2004-531337 | 10/2004 |
| JP | 2008-142563 | 6/2008 |
| JP | 2008-514307 | 8/2008 |
| WO | WO 00/60995 | 10/2000 |
| WO | WO 01/26557 | 4/2001 |
| WO | WO 01 /070116 | 9/2001 |
| WO | WO 02/034167 | 5/2002 |
| WO | WO 03/049619 | 6/2003 |
| WO | WO 2004/012583 | 2/2004 |
| WO | WO 2005/058239 | 6/2005 |
| WO | WO 2007/011994 | 1/2007 |
| WO | WO 2011/116379 | 9/2011 |
| WO | WO 2014/138284 | 9/2014 |
| WO | WO 2014/138482 | 9/2014 |
| WO | WO 2016/040526 | 3/2016 |
| WO | WO 2016/077783 | 5/2016 |
| WO | WO 2017/015632 | 1/2017 |
| WO | WO 2018/140535 | 8/2018 |
| WO | WO 2019/152598 | 8/2019 |
| WO | WO 2022/266022 | 12/2022 |

OTHER PUBLICATIONS

Black MD, M., Division of Pediatric Cardiac Surgery, Standford University School of Medicine, California, USA, Minimally Invasive Pediatric Cardiac Surgery, Online Article in 4 pages.

Ethicon Wound Closure Manual—Chapter 6, Research and Development at Ethicon, Inc.—An Ongoing Process of Change and Improvement, Online at www.ethiconinc.com in 4 pages.

Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.

Perclose A-T, 6F Suture-Mediated Closure (SMC) System, Instructions for Use disctributed in the U.S. by Abbott laboratories, Inc. 2002, 2006 Abbott Laboratories in 11 pages.

Quealy et al., "Use of Combined Intravascular Ultrasound and PTCA Catheter: Clinical Utility", Chapter 12, pp. 245-250.

International Search Report and Written Opinion issued in PCT Application No. PCT/US2016/043750, dated Oct. 19, 2016, in 19 pages.

International Search Report and Written Opinion issued in PCT Application No. PCT/US2018/015105, dated May 21, 2018, in 15 pages.

* cited by examiner

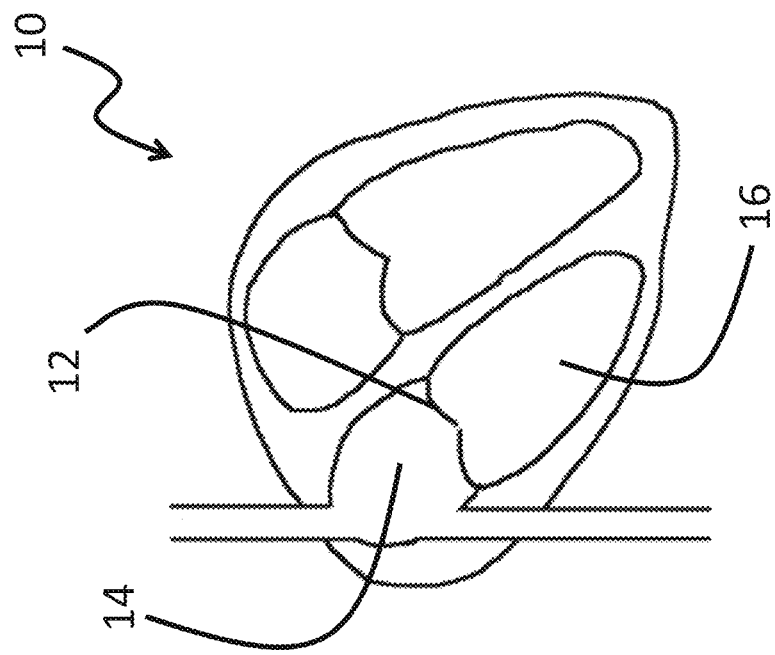
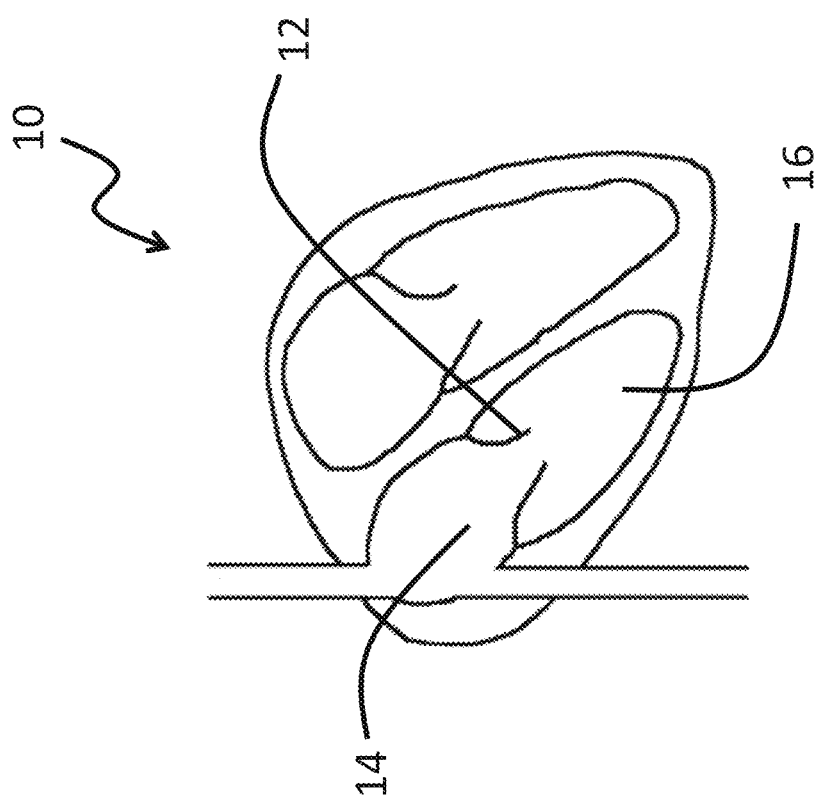
FIG. 1A
FIG. 1B

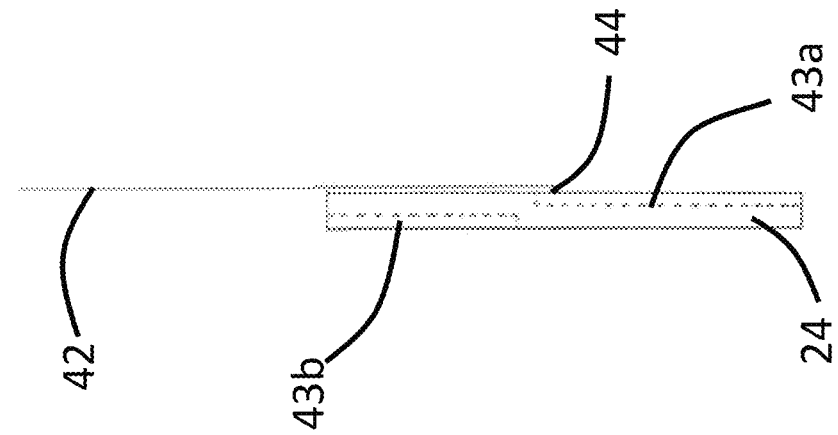
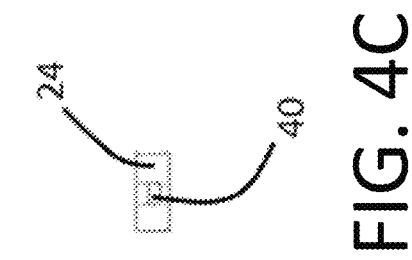
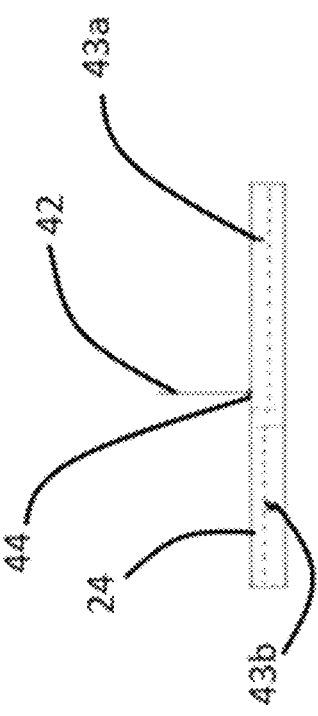

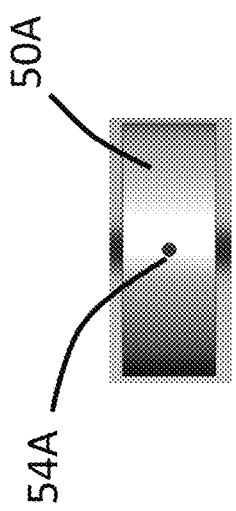
FIG. 6B
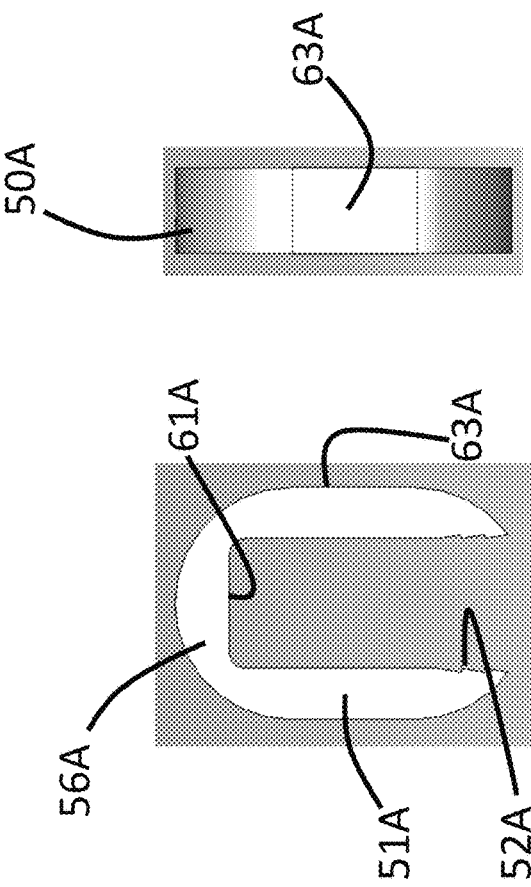
FIG. 6D
FIG. 6C
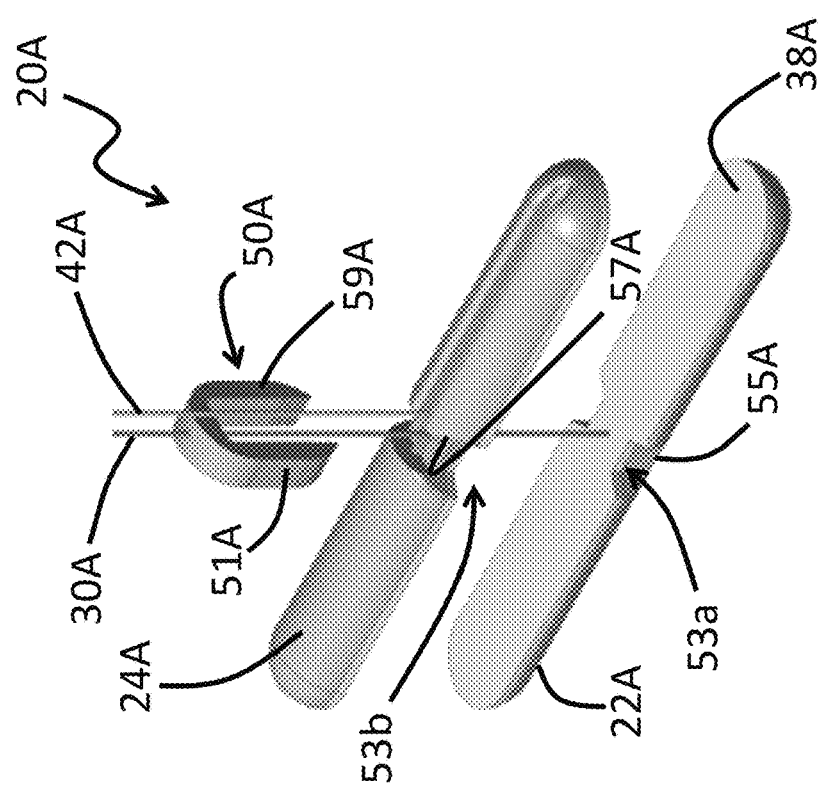
FIG. 6A

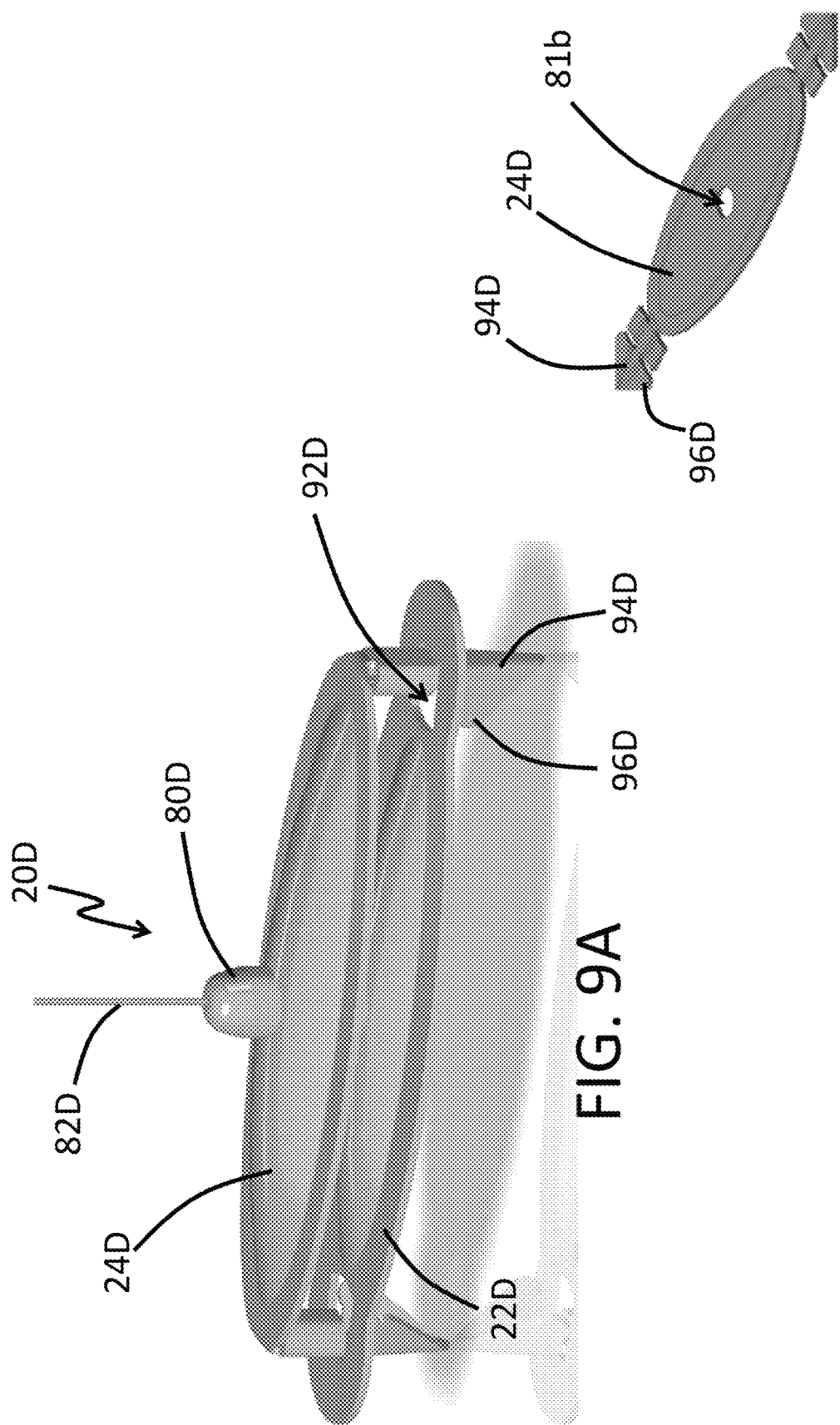

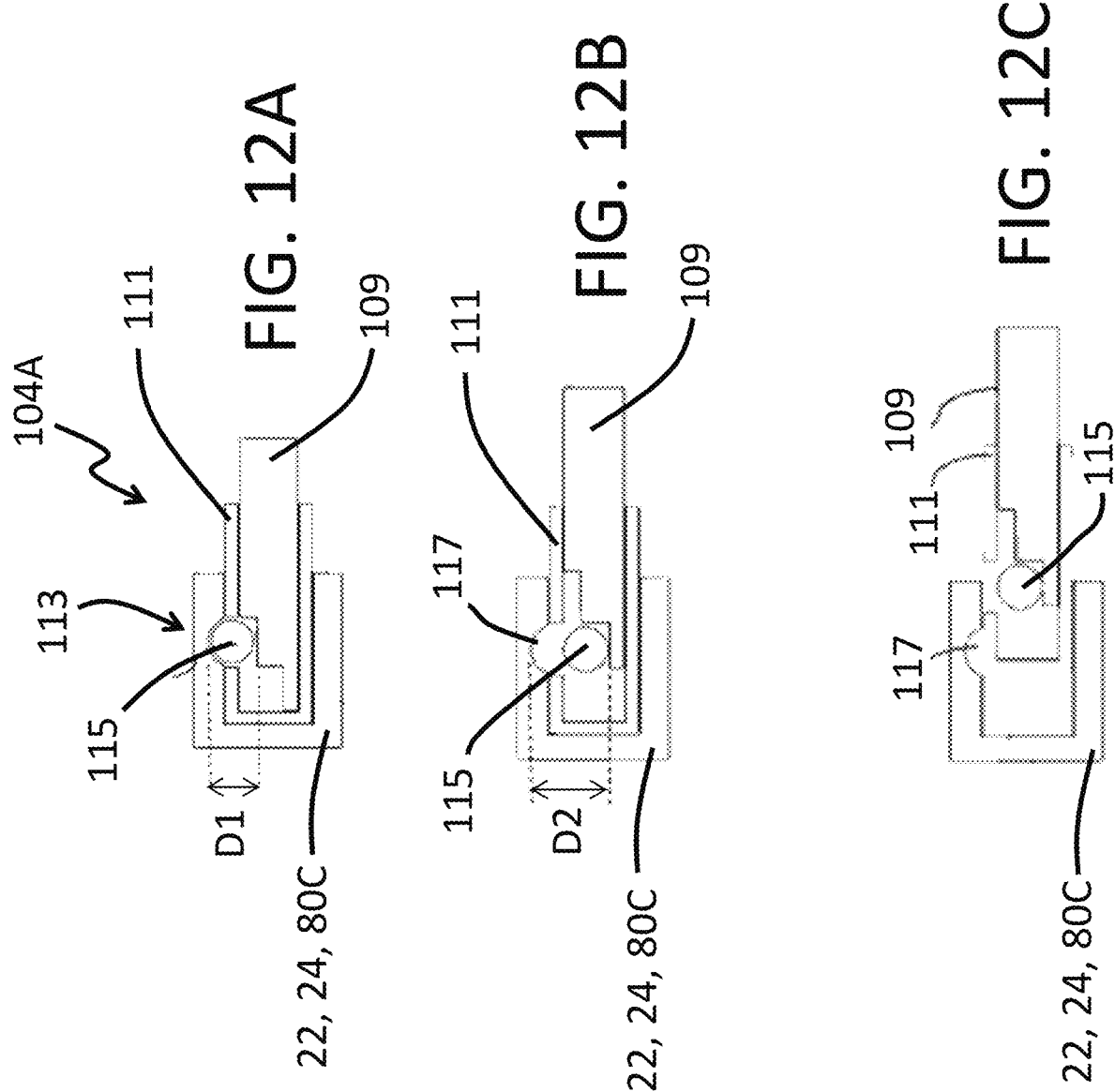

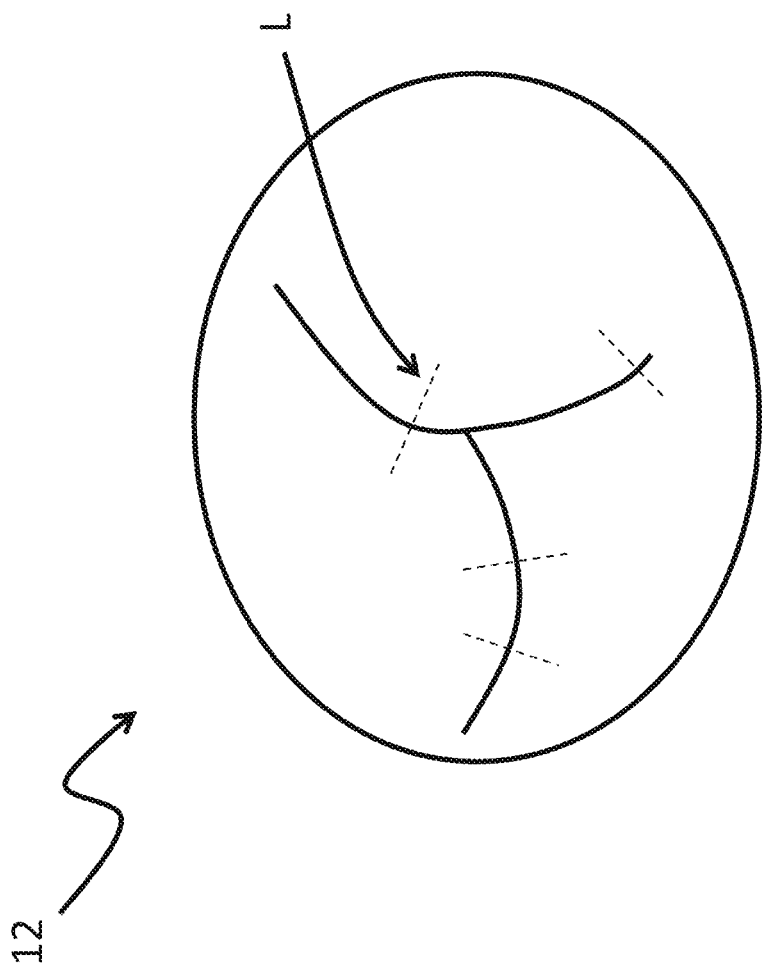

DEVICE FOR SECURING HEART VALVE LEAFLETS

CROSS-REFERENCE

This application is a continuation of U.S. patent application Ser. No. 15/746,788, filed Jan. 22, 2018, which is a National Phase of PCT Application No. PCT/US2016/043750, filed Jul. 22, 2016, which claims the benefit of U.S. Provisional Application No. 62/196,276, filed Jul. 23, 2015. Each of the foregoing applications is hereby incorporated by reference in its entirety herein.

BACKGROUND

Technical Field

The present disclosure relates to devices and methods for treating regurgitation in a heart valve.

Description of the Related Art

The tricuspid valve separates the right lower heart chamber (the right ventricle) from the right upper heart chamber (right atrium). Tricuspid regurgitation is a disorder in which this valve does not close tight enough. This problem causes blood to flow backward into the right upper heart chamber (atrium) when the right lower heart chamber (ventricle) contracts. Tricuspid regurgitation is leakage of blood backwards through the tricuspid valve each time the right ventricle contracts. Tricuspid regurgitation usually results from an enlarged lower heart chamber (called the ventricle) or from any other condition that constrains the blood flow from the right ventricle to the lungs. Sometimes long-standing disorders, such as emphysema or pulmonary stenosis can cause problems that affect the tricuspid valve which is "upstream" from the lungs. To compensate, the right ventricle enlarges so that it can pump harder, which sometimes causes the tricuspid opening to become stretched out and floppy. When valve disease is severe, it may be necessary to repair or replace the diseased valve. Valve repair is the most common surgical treatment for tricuspid valve disease. Tricuspid valve repair can be done alone or in combination with treatments for other heart problems.

Tricuspid valve repair using an annuloplasty ring is a common surgical approach for tricuspid regurgitation and may be performed for primary tricuspid disease or for combined cases with other valve surgery (mitral, aortic). Traditional tricuspid valve repair is an open-heart procedure performed through a 6-8 inch incision through the breastbone (sternum).

SUMMARY

For these reasons, there exists a need for minimally invasive methods of tricuspid valve repair. The present disclosure is directed to valve fixation devices that can be delivered endovascularly.

In one embodiment, a system is provided for delivering a distal plate to the ventricular side of the tricuspid valve and a proximal plate to the atrial side of the tricuspid valve. The system includes both tension guidewires and rigid catheters that allow positioning of the plates. The plates include slots that align to form a passage way between the plates. The system includes a locking clip having an end that is configured to pass through slots, or over the outer edges, of the plates. The locking clip is delivered along the guidewires until the end of the locking clip passes through the slots. The end of the locking clip is barbed or otherwise is configured to prevent the locking clip from separating from or backing off of the plates.

In one embodiment, the system includes a guidance rail that is used to deliver the fixation device to the tricuspid valve. Optionally, the guidance rail has a threaded tip that bores into the ventricular wall. In some embodiments, the guidance rail has a suction tip that reversibly holds the guidance rail to the ventricular wall. In some embodiments, the guidance rail is established by advancing a distal portion of the guidance rail into the pulmonary artery. In some embodiments, the distal portion of the guidance rail is floated into the pulmonary artery using a balloon-tipped guidewire.

In some aspects, the device is a heart valve prosthesis that has a distal member, a proximal member, and a connector. The distal member is configured to be advanced into a first heart chamber. The proximal member is configured to be advanced into a second heart chamber. The distal member and the proximal member each has a central portion disposed adjacent to a line of coaptation of two adjacent heart leaflets. The distal member and the proximal member each has peripheral portions that are placed into direct contact with the two adjacent heart leaflets. The proximal member is separate from the distal member and the central portions of the distal and proximal members are moveable relative to each other. The connector is configured to be disposed across a gap between the distal and proximal members to secure the central portion of the distal member to the central portion of the proximal member.

In some aspects, the connector is a locking clip that has an open end and a closed end. The open end is adapted to be advanced initially over the proximal member and subsequently over the distal member to secure the central portion of the distal member to the central portion of the proximal member. In certain aspects, the locking clip has an aperture sized to receive a guidewire that is connected with the distal member. In some aspects, the locking clip has a first aperture and a tracking feature. The first aperture is sized to receive a first guidewire that is coupled to the distal member. The tracking feature is sized to contact a second guidewire that is coupled to the proximal member. In some aspects, the tracking feature is a second aperture in the closed end of the locking clip.

In some aspects, at least one of the central portion of the distal member and the central portion of the proximal member includes a recess in which the connector can be disposed to provide a continuous periphery along at least one peripheral edge of the prosthesis. In some aspects, the proximal member has a channel disposed along a longitudinal axis of the proximal member. The channel is sized to receive a portion of a guidewire when the proximal member is in a low-profile configuration. In some embodiments, the channel extends along the peripheral portions on both sides of the central portion of the proximal member.

In some aspects, the connector has a first edge, a second edge, and a single guidewire aperture disposed between the first edge and the second edge. The second edge is disposed between the single guidewire aperture and a guidewire extending from the proximal member.

In some aspects, the connector has a first end, a second end, and an elongate body disposed between the first and second ends. The first end is configured to couple with a guidewire. The second end is configured to be disposed away from the first end. The elongate body is configured to slideably receive the distal member and the proximal member after the connector has been advanced into the patient.

In some embodiments, the distal member has a sheet-like configuration. The central portion of the distal member has an aperture sized to be slideable over the elongate body of the connector. In some aspects, the first end of the connector has a projection that is adapted to engage a mating feature on the distal member. The projection and the mating feature are configured so that torque applied to the connector causes rotation of the distal member about an axis that extends through the aperture of the distal member. The axis is oriented perpendicular to the aperture.

In some aspects, the central portion of the proximal member has an aperture configured to be advanced over the second end of the connector. The aperture is configured to lock to the connector as the proximal member is advanced from the second end of the connector toward the first end of the connector. In some aspects, the peripheral portion of one of the distal member or the proximal member has a locking aperture. The peripheral portion of the other member has a locking device that is configured to be advanced through the locking aperture to secure the distal member to the proximal member. In some aspects, the central portion of at least one of the distal and proximal members has a tubular body and the peripheral portions thereof comprise a curvature corresponding to a curvature of the tubular body at least in a delivery state.

In some aspects, the prosthesis further comprises a locking device configured to be advanced over the second end of the connector to releasably couple the proximal member to the connector. In some aspects, the peripheral portions of at least one of the distal and proximal members is adapted to transition from a low-profile tubular configuration to a plate-like configuration for engaging a corresponding leaflet. In some aspects, a leaflet facing side of at least one peripheral portion of at least one of the distal member and the proximal member has a barb oriented toward the central portion thereof. In some aspects, at least one surface of at least one of the distal member and the proximal member includes a pledget.

In some aspects, a system for treating heart valve insufficiency includes the heart valve prosthesis of any of the aspects previously described, and an anchor for securing a guidance rail to an internal surface of the heart. The anchor can have a threaded member. The anchor can have a suction tip.

In some aspects, a system for treating heart valve insufficiency can include the heart valve prosthesis of any of the aspects previously described, and a catheter assembly. The catheter assembly can include an outer body and an inner body. The outer body is configured to permit delivery of the distal member, the proximal member and the connector. The inner body is configured to direct a force to the proximal member in connection with moving the distal member and the proximal member toward each other.

In some aspects, a system for securing a leaflet of a heart valve includes a distal plate, a proximal plate, and a locking clip. The system can further include a pledget. The system can further include a guidance rail. The guidance rail can further include a suction tip.

In some aspects a method of performing a procedure in the heart includes providing a delivery catheter to a heart; passing a distal plate through the delivery catheter and into a right ventricle of the heart; drawing the distal plate against a leaflet of a tricuspid valve; passing a proximal plate through the delivery catheter and into a right atrium of the heart; positioning the distal and proximal plates such that the leaflet of the tricuspid valve is compressed between the distal and proximal plates; aligning the distal and proximal plates; and advancing a first end of a locking clip across the distal and proximal plates, thereby securing the distal plate to the proximal plate. Aligning the distal and proximal plates can further include moving one or both of the distal and proximal plates such that a passageway is disposed across the distal and proximal plates. In some aspects, the passageway includes a first slot or recess in the distal plate that aligns with a second slot or recess in the proximal plate. In some aspects, the locking clip is advanced into the right ventricle prior to passing the proximal plate into the right ventricle. In some aspects, the locking clip is advanced into the right atrium after passing the proximal plate into the right atrium.

The method can further include passing a guidance rail through the delivery catheter and into a right ventricle of the heart, wherein a distal portion of the guidance rail extends into a main pulmonary artery. The method can further include passing a guidance rail through the delivery catheter and into a right ventricle of the heart, a distal end of the guidance rail comprising a stabilization feature; and attaching the stabilization feature to a wall of the right ventricle. In some aspects, the stabilization feature is selected from the group consisting of a barbed tip, a threaded tip, and a suction tip. In some aspects, the distal plate is advanced over a first guidewire, the proximal plate is advanced over a second guidewire, with the first guidewire being spaced apart from the second guidewire. In some aspects, the proximal face of the proximal plate has a first groove that overlaps a second groove on a distal face of the proximal plate to form a passageway for a guidewire along a length of the proximal plate. In some aspects, the first guidewire is disposed in the passageway when the proximal plate is being advanced into the right atrium.

In some aspects, the method includes passing a locking nut through the delivery catheter and securing the locking nut to the first end of the locking clip. In some aspects, the distal plate is in a low-profile state during at least a portion of the passing, and the distal plate is in a deployed state during at least a portion of the drawing step.

In some aspects, the device is a heart valve prosthesis having a connector, a distal plate, and a proximal plate. The connector has a body that extends between a distal end and a proximal end of the connector. The proximal end has an opening sized to receive a guidewire into the body. The distal member is configured to be advanced into a first heart chamber and has a retention feature disposed on a central portion of the distal member. The retention feature is configured to prevent the distal end of the connector from passing beyond the distal member in a proximal direction. The proximal member is configured to be advanced into a second heart chamber. The proximal member has a second central portion configured to allow the proximal end of the connector to extend proximally beyond the proximal member. The first and second central portions are moveable relative to each other.

In some aspects, the heart valve has a locking feature configured to prevent the proximal end from moving through the second central portion in a distal direction after the locking feature has passed beyond the second central portion in the proximal direction. In some aspects, the locking feature comprises a push nut. In certain aspects, the distal and proximal members can move between a low-profile state and a deployed state, wherein compared to the low-profile state, in the deployed state at least a portion of the distal and proximal members is located further from the body of the connector.

In some aspects, at least one of the distal and proximal members comprises nitinol. In some aspects, the connector includes a protrusion configured to engage a recess on the distal member to prevent rotation of the distal member relative to the connector. In some aspects, the distal end of the connector has an opening aligned with the opening at the proximal end of the connector such that a guidewire can pass through the body of the connector. In some aspects, at least one of a distal face of the proximal member or a proximal face of the distal member includes a feature for piercing tissue disposed between the distal and proximal members.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 1A depicts a cross-sectional view of a heart in normal diastole.

FIG. 1B depicts a cross-sectional view of a heart in normal systole.

FIG. 4A is a side view of a proximal plate.

FIG. 4B is a bottom view of a proximal plate.

FIG. 4C is an end view of a proximal plate.

FIG. 4D is a side view of the embodiment of the proximal plate depicted in FIG. 4A, with the proximal plate being actuated to a low profile configuration.

FIG. 6A is an isometric view of an embodiment of a fixation device.

FIG. 6B is a top view of an embodiment of a locking clip.

FIG. 6C is an end view of an embodiment of a locking clip.

FIG. 6D is a side view of an embodiment of a locking clip.

FIG. 9A is an isometric view of an embodiment of a fixation device.

FIG. 9B is an isometric view of the proximal plate of FIG. 9A in a low-profile configuration.

FIG. 12A is a side view of a guidewire detachment feature in the secured state.

FIG. 12B is a side view of the guidewire detachment feature of 12A in the released state.

FIG. 12C is a side view of the guidewire detachment feature of 12A in the detached state.

FIG. 19 is a top view of a tricuspid valve illustrating a non-limiting selection of locations for placement of the device across the valve leaflets.

FIG. 19C-1 is a cross-sectional view of a delivery system showing the internal arrangement of the device components within the distal end of the delivery system.

FIG. 19C-2 is a cross-sectional view of a delivery system showing the internal arrangement of the device components within the distal end of the delivery system.

More detailed descriptions of various embodiments of catheter based transapical delivery systems, components and methods useful to treat patients are set forth below.

DETAILED DESCRIPTION

This device represents an endovascular method of reducing tricuspid regurgitation in patients with severe tricuspid regurgitation. This device is intended to be delivered preferably through the right internal jugular vein due to anatomical considerations, but may also be delivered through the left internal jugular vein or via the inferior vena cava.

The working principle of this device is the reduction of tricuspid regurgitation through the fixation of tricuspid valve leaflet edges. FIG. 1A is a schematic representation of a heart 10 in normal diastole. FIG. 1B represents the heart 10 in normal systole. The heart 10 consists of four chambers and the tricuspid valve 12 is interposed between the right atrium 14 and the right ventricle 16.

The present disclosure may represent a single point fixation between two leaflet edges of either two or three leaflets, or complete edge to edge fixation of the coaptation edges of two or three leaflets, or some combination of these methods. The right internal jugular vein (not shown) is preferable for delivery due to its most direct placement above the tricuspid valve 12. However, the devices and methods herein disclosed may be delivered through the left internal jugular vein or the inferior vena cava.

Some aspects of the present disclosure encompass a method of delivering to the ventricular side of the tricuspid valve 12, and steering with a steerable catheter to the desired leaflet coaptation point, an anchor that can include an attached and externalized guidewire or suture that is configured to secure the coaptation edge of two tricuspid leaflets at the ventricular surface. The externalized guidewire or suture can possess sufficient torsional rigidity to allow rotational control of the distal anchor. Tension can then be applied through the attached guidewire or suture to the distal anchor in the ventricular to atrial direction so that the coaptation edge of the two leaflets of interest may be brought closer together or, in some cases, forced closed. A means of then securing the leaflet coaptation edges can then be employed to cause the two edges to become fixed together. This procedure can then be repeated as needed to reduce the amount of tricuspid regurgitation.

Figure 2:
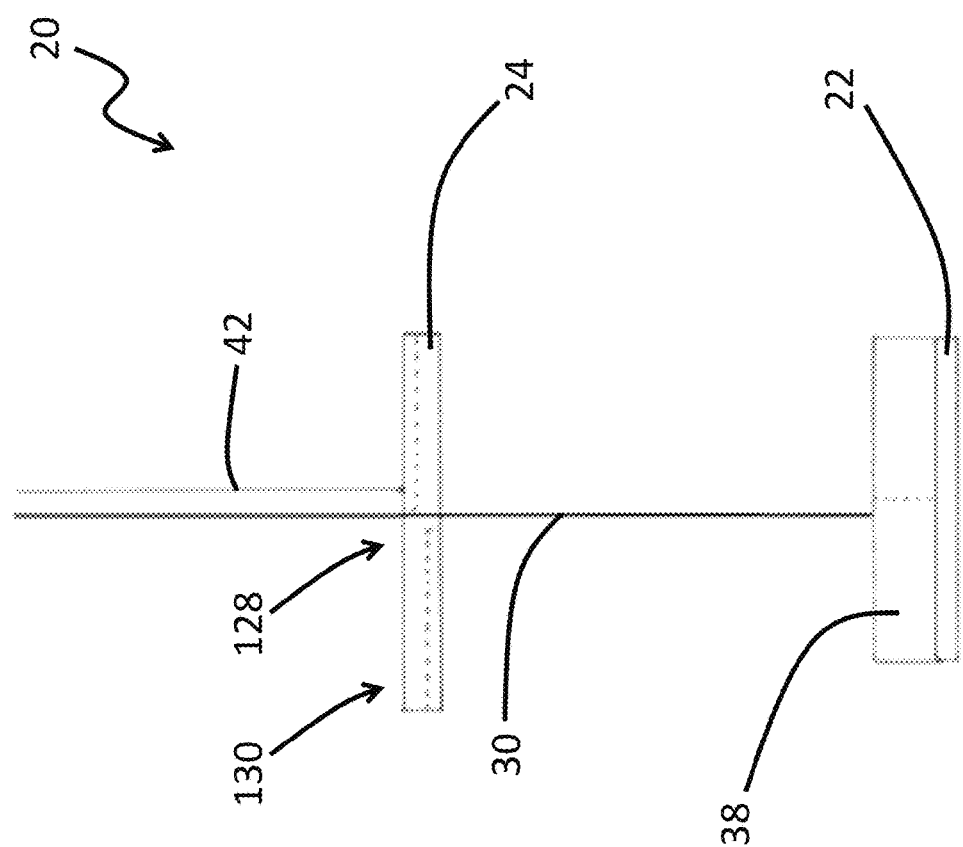
FIG. 2 depicts a side view of an embodiment of a fixation device.

FIG. 2 depicts a non-limiting exemplary embodiment of a device within the scope of the present disclosure. In various embodiments herein, the device 20 and variations discussed below can comprise a heart valve prosthesis. The device 20 can include two rigid or semi-rigid plates, referred to as the distal plate 22 and the proximal plate 24. In some aspects, the distal and proximal plates 22, 24 can sandwich the tricuspid leaflet edges and cause the entrapped edges to become fixed together. The distal and proximal plates 22, 24 can have a central portion 128 and a peripheral portion 130. In some configurations, the tricuspid leaflet edges are held between the peripheral portions 130 of the distal and proximal plates 22, 24, while the central portion 128 of the plates 22, 24 are secured together by a connector 126 (shown in FIG. 5B). The connector 126 can be disposed across a gap between the distal and proximal plates 22, 24. In some configurations, the distal and proximal plates 22, 24 can be aligned using alignment features (not shown), and locked together with a locking clip (shown in FIGS. 5A-C), thereby forming a durable fixation device. The distal and proximal plates 22, 24 may or may not feature a lengthwise curvature (not shown) as in a leaf spring to cause additional spring force to act to secure the leaflet between the plates.

Figure 3C:
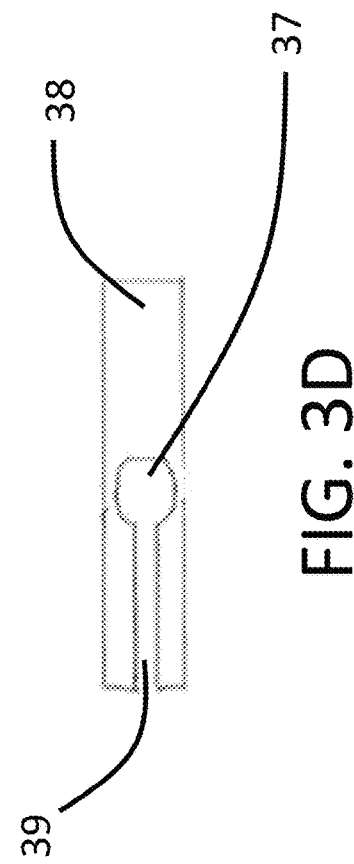
FIG. 3C is a side view of the embodiment depicted in FIG. 3A, with an addition of a pledget intended to contact the tricuspid valve.
Figure 3A:
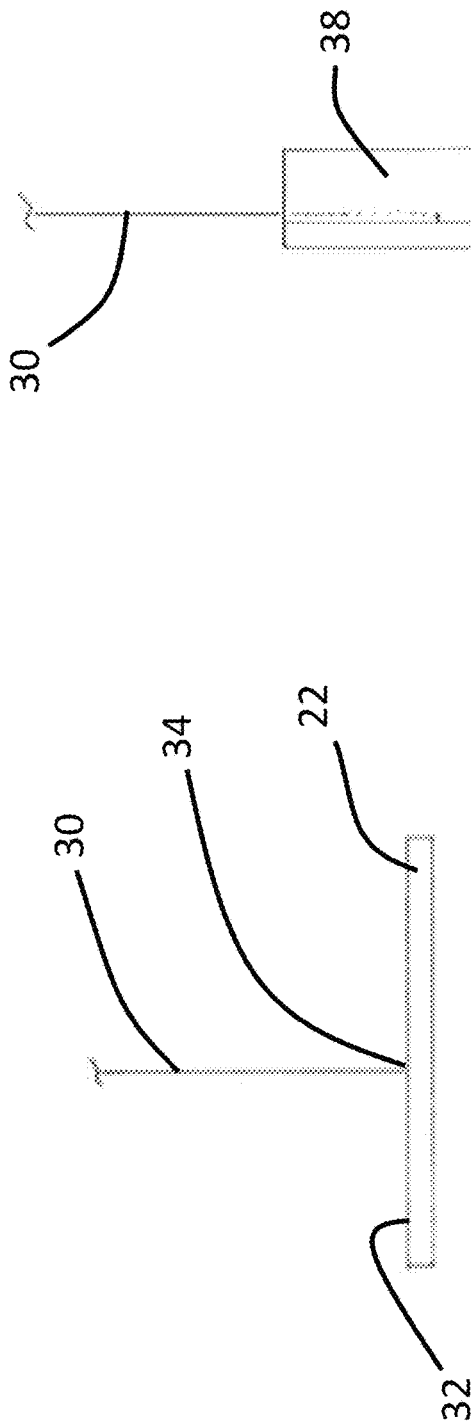
FIG. 3A shows a side view of an embodiment of a distal plate.
Figure 3D:
FIG. 3D is a top view of an embodiment of a pledget.
Figure 3B:
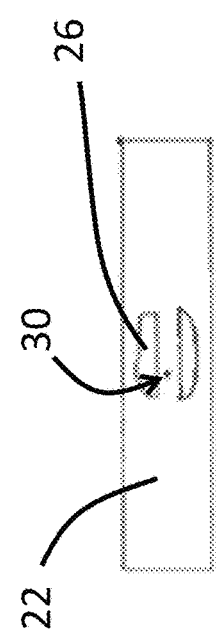
FIG. 3B shows a top view of an embodiment of a distal plate in a low-profile configuration.

FIGS. 3A and 3B depict a side view and a top view of a non-limiting exemplary embodiment of a distal plate 22. The distal plate 22 can be a rectangular plate comprised of metal (e.g., stainless steel, titanium, or titanium-containing alloy) or polymer. The distal plate 22 may incorporate slots 26 that facilitate alignment and fixation with the proximal plate 24. A distal guidewire 30 or suture that is externalized from the patient may be attached to the distal plate 22 to allow traction to be applied to the distal plate 22. The distal guidewire 30 can be configured to provide rotational control of the distal plate 22. The distal plate 22 may or may not include a compliant material layer (not shown) bonded to the surface 32 of the distal plate 22 at the point of contact with the tricuspid leaflets. The distal guidewire 30 or suture can be mounted slightly off center along the long axis of the distal plate 22 on a pivoting anchor 34, which can allow the distal plate 22 to be rotated such that its long axis is parallel to the distal guidewire 30 or suture. FIG. 3C shows a side view of the distal plate 22 rotated such that its long axis is parallel to the distal guidewire 30. In some aspects, the distal plate 22 may interface with a pledget 38. A non-limiting exemplary embodiment of a pledget 38 is shown in FIG. 3C and is discussed below. The distal plate 22 may provide a sturdy mechanical backing for the pledget 38.

FIG. 3D depicts a top view of a non-limiting exemplary embodiment of a pledget 38. The pledget 38 can be made of woven or non-woven fibrous material such as Dacron or Gore-Tex or a bulk material such as silicone rubber. The pledget 38 can include a notch 39 cut into the material to allow the distal guidewire 30 to fold flat against the distal plate 22 as shown in FIG. 3C. The pledget 38 can be configured to enhance securement of the tricuspid valve between the distal and proximal plates 22, 24. In some aspects, the pledget 38 may act as a cushion. The pledget 38 may receive spikes on the proximal plate 24 that pass through the valve leaflet and penetrate the pledget 38 as the proximal plate 24 is pushed toward the distal plate 22. In some configurations, the locking clip passes through a circular cut-out 37 of the pledget 38. The locking clip clips completely outside the perimeter of the plates in one embodiment. Some embodiments incorporate a clip that penetrates the pledget 38.

FIGS. 4A-C depict a side view, a bottom view, and an end view of a non-limiting exemplary embodiment of a proximal plate 24. The proximal plate 24 can be a rectangular plate comprised of metal or polymer. The proximal plate 24 may incorporate a protruding feature (not shown) that mates and self-aligns with the distal plate 22. The proximal plate 24 may include slots 36 that align with the slots 26 of the distal plate 22, thereby facilitating the passage of a barbed locking clip to fix the distal and proximal plates 22, 24 together. The proximal plate 24 can include a feature 40 (e.g., through hole) to allow passage of the distal guidewire 30 or suture from the distal plate 22. The proximal plate 24 may have an affixed proximal guidewire 42 or suture that is externalized from the patient to allow traction and rotational control to be applied to the proximal plate 24. The proximal guidewire 42 or suture can be mounted centrally on the proximal plate 22 on a pivoting anchor 44. The pivoting anchor 44 may be configured to allow the proximal plate 24 to be rotated such that its long axis is parallel to the proximal guidewire 42 or suture, as shown in FIG. 4D. A friction enhancing feature such as a series of teeth, bumps, or surface roughening may or may not be applied to the surface of the distal or proximal plate 22, 24 that contacts the tricuspid leaflets. The proximal plate 24 can include one or more grooves 43 a,b. The grooves 43 a,b can extend more than halfway across the distal plate 24 and overlap with one another so that when the proximal plate 24 and its guidewire 42 are in the deployed configuration (i.e., long axis of the proximal plate 24 is perpendicular to the proximal guidewire 42), there exists a hole 40 through which the proximal end of the distal guidewire 30 can be threaded. When the proximal plate 24 is in the folded configuration (i.e., long axis of the proximal plate 24 is parallel to its guidewire 42), the grooves 43 a,b can allow the distal guidewire 30 to clear the ends of the proximal plate 24. When the proximal plate 24 is viewed end-on, the overlapping grooves 43 a,b can form a through hole that allows the proximal plate 24 to be advanced lengthwise over the distal guidewire 30, through a catheter, to the right atrium where the proximal plate 24 can be rotated 90 degrees relative to the proximal guidewire 42 to bring the proximal plate 24 into the deployed configuration. The slot configuration allows the distal guidewire 30 to clear the proximal plate 24 so that it now passes only through the hole 40.

Figure 5C:
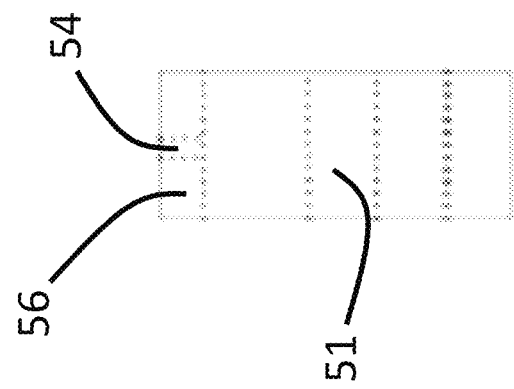
FIG. 5C is a side view of an embodiment of a locking clip.
Figure 5A:
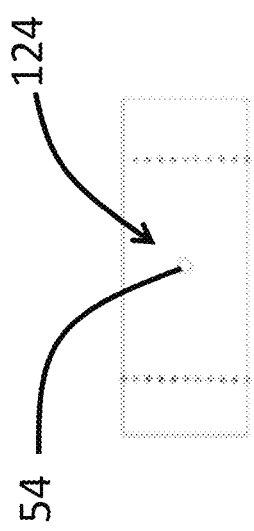
FIG. 5A is a top view of an embodiment of a locking clip.
Figure 5B:
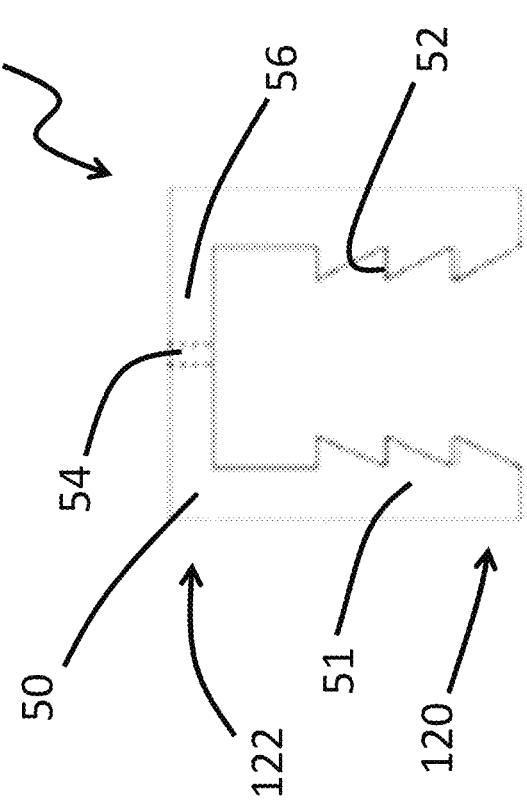
FIG. 5B is an end view of an embodiment of a locking clip.

FIGS. 5A-C depict a top view, an end view, and a side view of a non-limiting exemplary embodiment of a connector 126. The connector 126 can be a locking clip 50. The locking clip 50 can be a rigid part made of metal or polymer. The locking clip 50 may include an open end 120 and a closed end 122. As described below, the open end 120 can be advanced initially over the proximal plate 24 and subsequently over the distal plate 22. The locking clip may include spaced apart arms 51 that extend from a bridge portion 56. The arms 51 can include raised features 52 that can be threaded through the concentric slots 26, 36 of the distal and proximal plates 22, 24. In some configurations, the arms 51 can be pushed over the edges of the distal and proximal plates 22, 24, as described below. The connector 126 can include an aperture 124 configured to receive a guidewire. The locking clip 50 can include a central hole 54 to allow passage of the distal and proximal guidewires 30, 42 that connect to the distal and proximal plates 22, 24. The raised features 52 may incorporate a series of barbs on the ends such that passage of the locking clip 50 through the distal and proximal plates 22, 24 can proceed in one direction only. The bridge portion 56 prevents the locking clip 50 from passing through the concentric slots 26, 36 of the distal and proximal plates 22, 24. The bridge portion 56 of the locking clip 50 may also integrate a compliant material where the locking clip 50 contacts the proximal plate 24. The compliant material can act as a spring to push the proximal plate 24 against the distal plate 22. In some aspects of the present disclosure, when the barbed ends of the raised features 52 are threaded through the concentric slots 26, 36, the barbs grip the ventricular side of the distal plate 22, thereby causing the bridge portion 56 to apply a retaining force against the atrial side of the proximal plate 22, the effect of which is similar to a rivet holding the distal and proximal plates 22, 24 together. Additionally and alternatively, the locking clip 50 can be a U-shaped part featuring barbed ends that fasten externally over the distal and proximal plates 22, 24.

FIG. 6A depicts an embodiment of a device 20A that is similar to the device 20 except as described differently below. The features of the device 20A can be combined or included with the device 20 or any other embodiment discussed herein. The device 20A can comprise a heart valve prosthesis. The device 20A has a locking clip 50A that fastens externally to the periphery of the distal and proximal plates 22A, 24A. In the illustrated embodiment, the distal and proximal plates 22A, 24A each have a narrows 53a, 53b. The transverse width of the distal and proximal plates 22A, 24A is reduced at the narrows 53a, 53b, as shown in FIG. 6A. The locking clip 50A can be advanced along the distal guidewire 30A so that the arms 51A of the locking clip 50A extend through the narrows 53a, 53b and across the distal and proximal plates 22A, 24A. In the illustrated embodiment, the distal guidewire 30A passes through a central hole 54A of the locking clip 50A, and the proximal guidewire 42A does not pass through the locking clip 50A. In some embodiments, the proximal guidewire 42A is disposed laterally outward of an end surface 57A of the narrows 53b. In other words, the end surface 57A of the narrows 53b of the proximal clip 24A can be disposed between the proximal guidewire 42A and a face 59A of the locking clip 50A. As discussed, the distal and proximal plates 22A, 24A can include a pledget 38A. The illustrated embodiment shows that the pledget 38A can be substantially uniform across the face of the plate and need not have a groove 39 (shown in FIG. 3D).

The locking clip 50A can have a thickness dimension that is oriented normal to the face 59A. In other words, FIG. 6A shows the locking clip 50A oriented so that the thickness dimension of the locking clip 50A is aligned parallel with the longitudinal axis of the distal and proximal plates 22A, 24A. By positioning the proximal guidewire 42A outside of the locking clip 50A, the thickness of the locking clip 50A can be reduced. Reducing the thickness of the locking clip 50A can reduce backflow through the anchor point (e.g., the narrows 53a, 53b) when the locking clip 50A is secured to the valve leaflets. The locking clip 50A can have a width dimension that is oriented along a line that extends between the arms 51A of the locking clip 50A. The width of the locking clip 50A can be selected so that the side face 63A is substantially flush with the lateral portions of the distal and proximal plates 22A, 24A when the locking clip 50A is seated within the narrows 53a, 53b. The locking clip 50A can be adapted so that the outer surface of the locking clip 50A is substantially flush with the outer surface of the distal and proximal plates 22A, 24A when the locking clip 50A is seated within the narrows 53a, 53b to secure the distal and proximal plates 22A, 24A together, thereby giving the device 20A a smooth outer surface. The edges of the device 20A can be contoured to be smooth and rounded. In some configurations, the edges of the device are contoured (e.g., rounded) to avoid thrombosis.

Figure 6F:
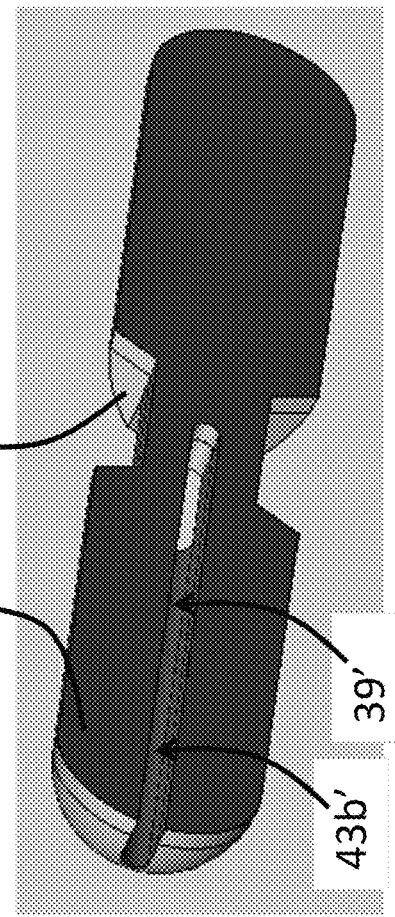
FIG. 6F is a partial bottom view of the proximal plate of the fixation device of FIG. 6A.
Figure 6E:
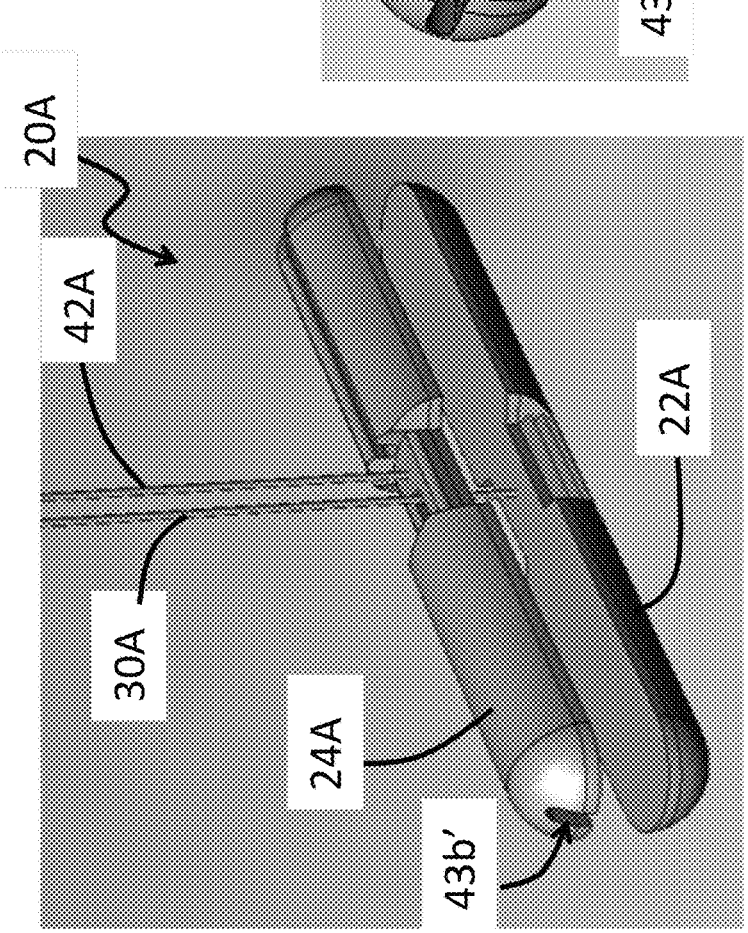
FIG. 6E is an isometric view of the fixation device of FIG. 6A.

FIGS. 6B-6D show a top view, an end view, and a side view of the locking clip 50A depicted in FIG. 6A. The locking clip 50A can be laser cut from flat sheet material for ease of manufacturing. As described above, the arms 51A of the locking clip 50A can have a raised feature 52A that engages with the edge of the distal plate 22A. In the illustrated embodiment, the locking clip 50A has a raised feature 52A with a cam surface adapted to allow the raised feature 52A to be advanced distally over a ridge 55A within the narrows 53a of the distal plate 22A. The cam surface of the raised feature 52A cause the arms 51A of the locking clip 50A to deflect laterally away from the center line of the locking clip 50A as the locking clip 50A is advanced distally over the ridge 55A. Once the cam surface of the raised feature 52A clears the ridge 55A, the arms 51A of the locking clip 50A spring back toward the center line of the locking clip 50A, thereby securing the ridge 55A of the distal plate 22A behind a flat proximally-facing surface of the raised feature 52A and restricting movement of the locking clip 50A in the proximal direction. The locking clip 50A can be sized so that when the raised feature 52A is seated over the ridge 55A of the distal plate 22A, the under surface 61A of the bridge portion 56A compresses the proximal plate 24A toward the distal plate 22A. The locking clip 50A can be sized to compress a tissue (e.g., tricuspid valve leaflet) secured within the gap between the distal and proximal plates 22A, 24A. In some configurations, the locking clip 50A can be adapted to compress a tissue by about: 1%, 5%, 10%, 20%, and values therebetween. A compression of about 10% means that the thickness of the uncompressed tissue is 10% greater than the thickness of the compressed tissue. FIG. 6E shows an isometric view of the other end of the device 20A. FIG. 6F shows a bottom view of the proximal plate 24A. As discussed above, the proximal plate 24A can have a groove 43b' on the leaflet-facing surface of the proximal plate 24A. The groove 43b' can accommodate the distal guidewire 30A when the proximal plate 24A is in the low-profile configuration. As shown in FIG. 6F, the pledget 38A can have a groove 39' that aligns with the groove 43b' of the proximal plate 24A.

Figure 7D:
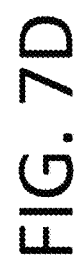
FIG. 7D is a side view of an embodiment of a locking clip.
Figure 7B:
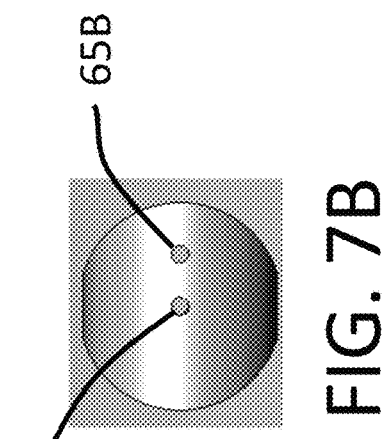
FIG. 7B is a top view of an embodiment of a locking clip.
Figure 7C:
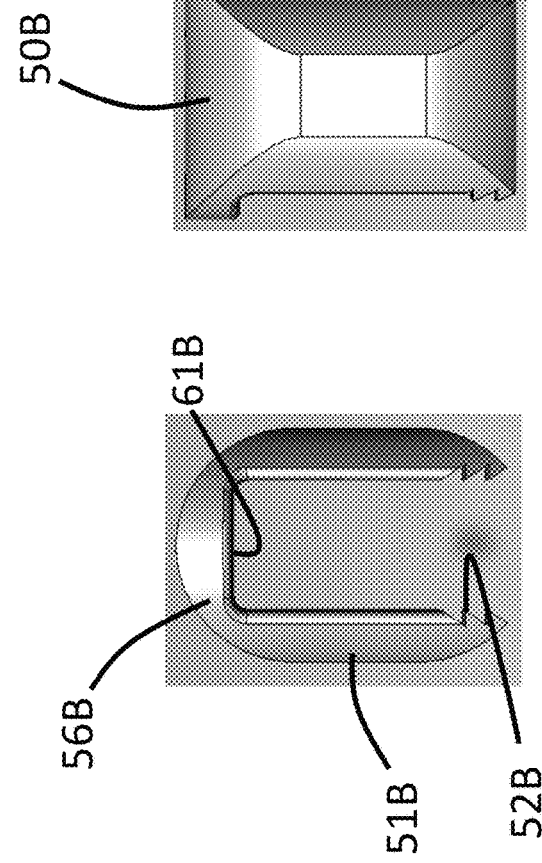
FIG. 7C is an end view of an embodiment of a locking clip.
Figure 7A:
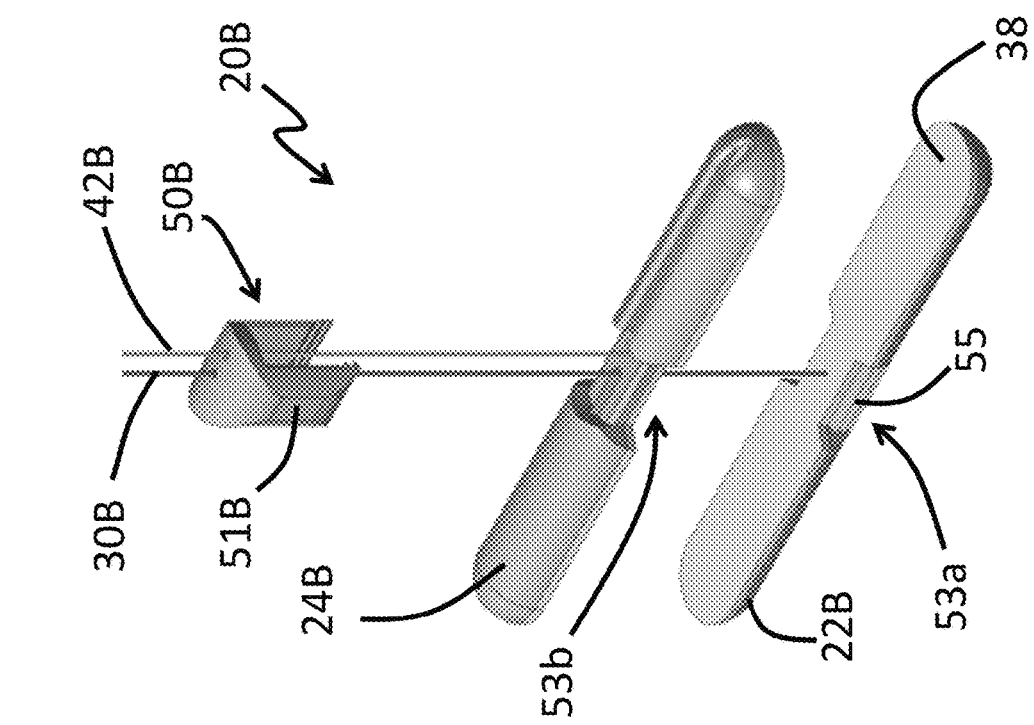
FIG. 7A is an isometric view of an embodiment of a fixation device.

FIG. 7A depicts an embodiment of a device 20B that is similar to the device 20 and to the device 20A except as described differently below. The features of the device 20B can be combined or included with the device 20, 20A or any other embodiment discussed herein. The device 20B can comprise a heart valve prosthesis. The device 20B has a locking clip 50B that fastens externally over the distal and proximal plates 22B, 24B. In the illustrated embodiment, the distal and proximal guidewires 30B, 42B pass through holes in the body of the locking clip 50B. As described above, the arms 51B of the locking clip 50B can extend over the periphery of the distal and proximal plates 22B, 24B. The arms 51B of the locking clip 50B can seat within the narrows 53a, 53b of the distal and proximal plates 22B, 24B. The locking clip 50B can be adapted so that the outer surface of the locking clip 50B is substantially flush with the outer surface of the distal and proximal plates 22B, 24B when the locking clip 50B is seated within the narrows 53a, 53b to secure the distal and proximal plates 22B, 24B together, thereby giving the device 20B a smooth outer surface.

FIGS. 7B-7D show a top view, an end view, and a side view of the locking clip 50B depicted in FIG. 7A. As shown in FIG. 7B, the locking clip 50B can have a first hole 63B and a second hole 65B. The distal guidewire 30B can pass through the first hole 63B. The proximal guidewire 42B can pass through the second hole 65B. As described above, the locking clip 50B can be adapted to compress a tissue secured within the gap between the distal and proximal plates 22B, 24B by about: 1%, 5%, 10%, 20%, and values therebetween.

In pre-delivery configuration, the distal plate 22 can be rotated about its attachment point to the distal guidewire 30 or suture, so that its long axis is parallel to the distal guidewire 30 or suture, and this assembly can be enclosed inside a delivery catheter. Likewise, the proximal plate 24 can be rotated about its attachment point to the proximal guidewire 42 or suture, so that its long axis is parallel to the proximal guidewire 42, also referred to as a traction wire 42 or suture, and this assembly is enclosed inside the same or a separate delivery catheter.

A method of placement of the distal and proximal plates 22, 24 or the plates 22B, 24B within a single delivery catheter is provided below. However, this method of device placement is presented for illustrative purposes only and is not to be taken as limiting. Indeed the other heart valve prosthesis devices disclosed herein can be deployed in similar methods. The steps are not all required, nor must they be performed in the order presented.

1. Place right internal jugular vein access sheath
2. Through this sheath, advance and steer the distal delivery catheter tip to just distal to the tricuspid valve.
3. Advance the distal plate, such as the plate 22B or any of the other distal plates beyond a delivery catheter 208 as shown in FIG. 19C-1 using the attached traction wire 30A.
4. Under fluoroscopic/echocardiographic guidance, position the distal plate 22B or any of the other distal plates parallel to the tricuspid valve plane coaptation line (perpendicular to its tension wire 30B).
5. Withdraw and park the tip of the delivery catheter 208 into the right atrium.
6. Adjust manual tension on the distal wire 30B, allowing the distal plate 22B to tent the tricuspid valve closed, and evaluate tricuspid regurgitation.
7. Advance the proximal plate 24B or any of the other proximal plates disclosed herein beyond delivery catheter 208 using the attached tension wire 42B
8. Apply manual tension on the proximal plate wire 42B so that proximal plate 24B is pulled back firmly against its delivery catheter 208, and positioned parallel to the plane of the tricuspid valve and coaptation line (perpendicular to its tension wire 42B).
9. Holding the proximal plate 24B against the delivery catheter 208, advance the delivery catheter 208 with proximal plate over the distal plate wire 30B. In the case of the embodiment of FIGS. 2-5C, if alignment features are present one can cause the raised proximal plate alignment features to mate with the distal plate slots.
10. Simultaneously pull on the distal plate tension wire 30B and push on the delivery catheter 208 to force the two plates 22B, 24B together, sandwiching and fixing the tricuspid valve leaflet edges.
11. Withdraw the delivery catheter, leaving the two tension wires in place. In one embodiment where the proximal plate has teeth that penetrate through the tricuspid valve and into a pledget backing material that is secured to the distal plate, the force of the pledget material on the proximal plate teeth can hold the leaflets together. In one embodiment, the distal plate, proximal plate, and locking clip are all enclosed in a single delivery catheter, once the proximal and distal plates are forced together, the locking clip can be advanced through the catheter to lock the proximal and distal plates together.
12. Advance the locking clip 50B over both tension wires 30B, 42B, and backed with a pushing catheter or distal plate 22B.
13. Simultaneously pull on the distal plate tension wire 30B and push on the pusher catheter 230 with locking clip 50B to secure the locking clip 50B, through the proximal plate 24B, to the distal plate 22B such that the raised features 52B of locking clip 50B which can be barbs are securely engage the distal plate 22B.
14. Withdraw locking clip pushing catheter 230, leaving the proximal and distal tension wires 30B, 42B in place.
15. Thread both tension wires 30B, 42B through a wire cutter, and advance the wire cutter over both wires 30B, 42B against the proximal end of the locking clip 50B.
16. Cut both tension wires 30B, 42B flush against the locking clip 50B, and withdraw the wire cutter and tension wire remnants. Alternatively to the wire cutter, devices for detaching the wires 30B, 42B can be as illustrated and described in connection with FIGS. 11A-12C.

17. Re-evaluate tricuspid regurgitation; if additional repairs are required, repeat steps 2-16 to perform any additional repairs.

18. If a suitable repair has been performed, remove the right internal jugular vein sheath, performing a vascular repair with a percutaneous closure device if required.

Figure 8B:
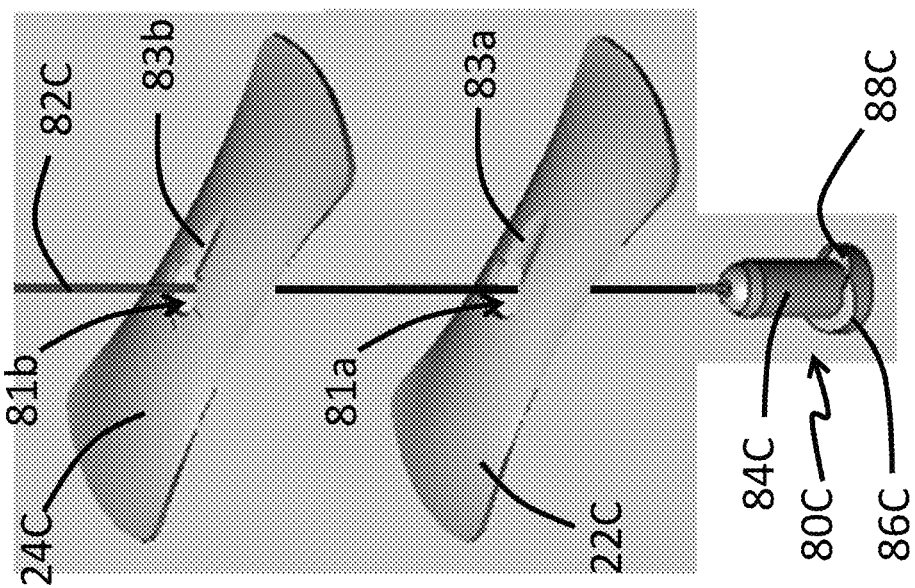
FIG. 8B is an exploded view of the fixation device of FIG. 8A.
Figure 8A:
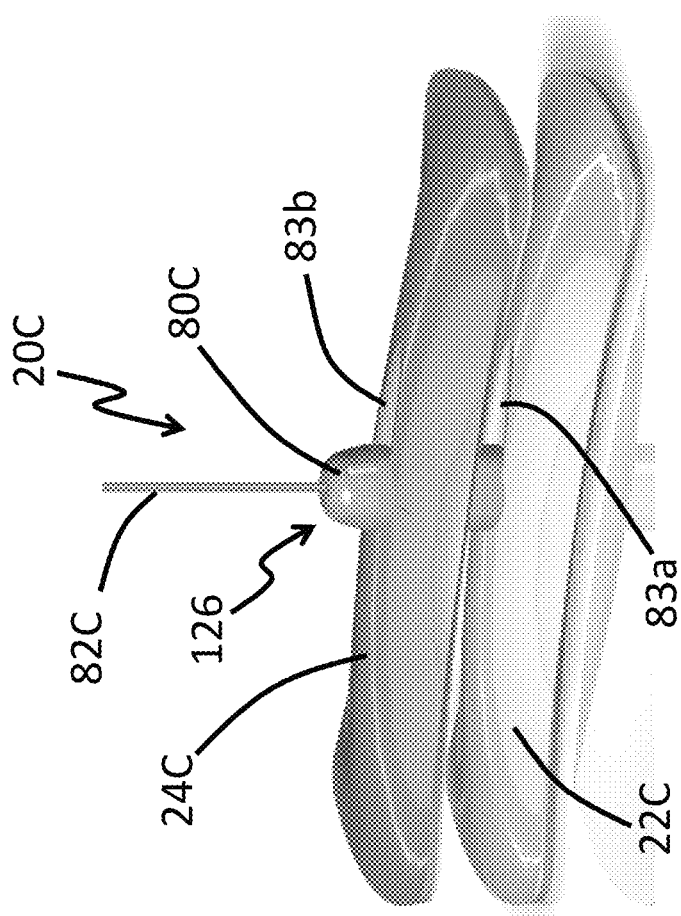
FIG. 8A is an isometric view of an embodiment of a fixation device.

FIG. 8A depicts an embodiment of a device 20C that is similar to the device 20 except as described differently below. The features of the device 20C can be combined or included with the device 20 or any other embodiment discussed herein. The device 20C can comprise a heart valve prosthesis. The device 20C comprises a connector 126 that is a locking pin 80C. The locking pin 80C can pass through a central opening in each of the distal and proximal plates 22C, 24C. The locking pin 80C can be coupled to a central guidewire 82C. In some configurations, the central guidewire 82C can be hollow, as discussed in more detail below. The central guidewire 82C can pass through central openings 81a, 81b (shown in FIG. 8B) of the distal and proximal plates 22C, 24C. As discussed below, the locking pin 80C can be configured to secure the distal plate 22C and the proximal plates 24C. For example, the locking pin 80C can have a deformable feature with a cam surface that deflects toward the central guidewire 82C as the locking pin 80C is pulled through the proximal plate 24C. Once the deformable feature passes through the central opening 81b of the proximal plate 24C, the deformable feature may spring away from the central guidewire 82C, thereby preventing the locking pin 80C from moving distally relative to the proximal plate 24C. In some embodiments, the locking pin 80C can be configured like a rivet. In some configurations, the locking pin 80C is configured so that the locking pin 80C can collapse under compression, causing at least a portion of the locking pin 80C to expand radially outward. The radially-expanded portion of the collapsed locking pin 80C can be sized to prevent the locking pin 80C from passing back through the central opening 81b in the distal direction. In some configurations, the locking pin 80C engages with one or both of the pates 22C, 24C in a manner similar to a push nut. An interference fit can be provided between one or both of the locking pin 80C and the plates 22C, 24C.

As discussed below, in some embodiments a reversible locking feature (e.g., threaded nut) can be used to secure the locking pin 80C to the distal and proximal plates 22C, 24C. For example, the proximal end of the locking pin 80C can have an external thread (not shown) that mates with the internal thread of a threaded nut (not shown). A pusher catheter can be used to advance the threaded nut along the central guidewire 82C. The threaded nut can include an interlock feature (e.g., recess) that mates to a corresponding feature (e.g., protrusion) on the pusher catheter, thereby allowing the pusher catheter to advance the thread nut along the central guidewire 82C. The interlock feature can be further adapted to allow the pusher catheter to rotate the threaded nut about the central guidewire 82C. In this way, the pusher catheter can be used to tighten or loosen the threaded nut onto the proximal end of the locking pin 80C.

The distal and proximal plates 22C, 24C can have a recess 83a, 83b. In some embodiments, the recess 83a, 83b is configured to interlock with the locking pin 80C. In some embodiments, the recess 83a, 83b is configured to accommodate the guidewire 82C when the plate 22C, 24C is folded parallel to the guidewire 82C to avoid the guidewire 82C being forced to make a kink as the guidewire 82C passes through a central opening 81a, 81b of the plate 22C, 24C.

FIG. 8B shows an exploded view of the device 20C, illustrating that the locking pin 80C can have a shaft 84C and a collar 86C. The locking pin 80C can be sized so that the shaft 84C can pass through a central opening 81a in the distal plate 22C and through a central opening 81b in the proximal plate 24C. The collar 86C can be adapted so that the collar 86C cannot pass through the central opening 81a of the distal plate 22C. In the illustrated embodiment, the collar 86C and the central opening 81a are both substantially axisymmetric. In some configurations, the collar 86C and the central opening 81a can be shaped so that the collar 86C can pass through the central opening 81a in some rotational configurations but cannot pass through the central opening 81a in other rotational configurations. For example, the collar 86C could have a protrusion (not shown) that can pass through the distal plate 22C only when the protrusion is aligned with a slot (not shown) that extends from the central opening 81a.

The distal and proximal plates 22C, 24C can be adapted to have a delivery configuration and a deployed configuration. For example, the distal and proximal plates 22C, 24C can be made of a compliant material (e.g., polymer) that can be elastically deformed into a low-profile configuration (e.g., rolled up) and stored within a sheath that holds the plates 22C, 24C in the low-profile configuration for delivery through a catheter. After the plates 22C, 24C reach a desired delivery location, the sheath can be retracted to expose the plates 22C, 24C, thereby allowing the plates 22C, 24C to move to the deployed configuration (e.g., unroll). In some embodiments, the distal and proximal plates 22C, 24C can comprise a shape memory material or super-elastic material (e.g., nitinol). In some embodiments, the distal and proximal plates 22C, 24C can have a contoured shape that provides stabilization of the plate in fluid flow. For example, the plate can be shaped so that the surface of the plate that is facing the valve leaflet aligns with a desired orientation (e.g., co-planar with the valve annulus) when blood is flowing past the plate. In some embodiments, the desired orientation to utilize flow to help stabilize the plates 22C, 22D is an inverted dome. In some configurations, the domed side (e.g., convex side) of the plate faces upstream, and the cupped side (e.g., concave side) faces downstream.

With continued reference to FIG. 8B, the locking pin 80C can include an interlock feature 88C that mates with a corresponding feature on the distal plate 22C. In the illustrated embodiment, the interlock feature 88C is a notch that has a proximal-facing concave surface. The curvature of the notch matches a corresponding convex surface disposed on the distal-facing surface of the distal plate 22C. The interlock feature 88C can hold the distal plate 22C rotationally fixed relative to the locking pin 80C. The interlock feature 88C can allow adjustment of the position of the distal plate 22C. For example, after the interlock 88C of the locking pin 80C mates with a corresponding feature on the distal plate 22C, rotation of the locking pin 80C can cause the distal plate 22C to rotate with the locking pin 80C. In some embodiments, the locking pin 80C can be rotated by rotating the central guidewire 82C.

Figure 8D:
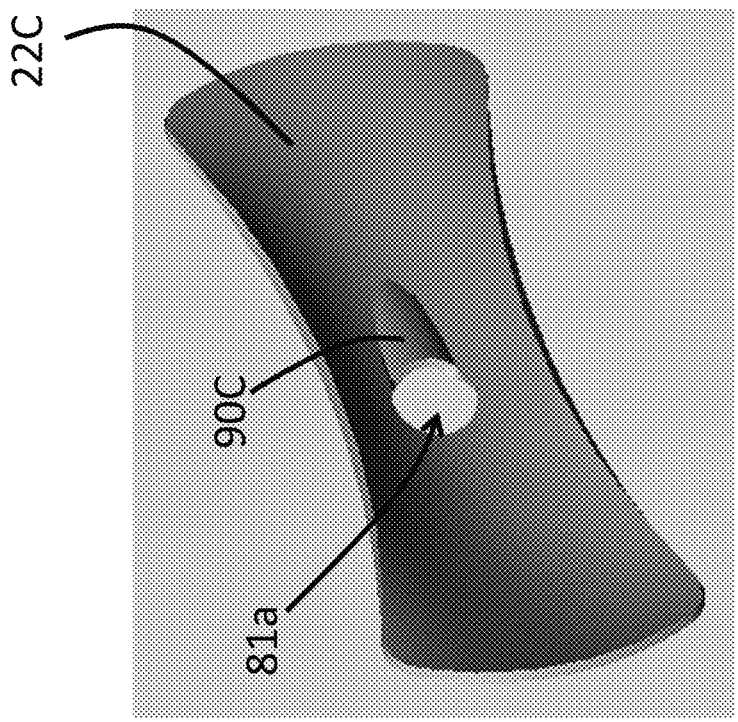
FIG. 8D is a bottom view of the distal plate of FIG. 8A.
Figure 8C:
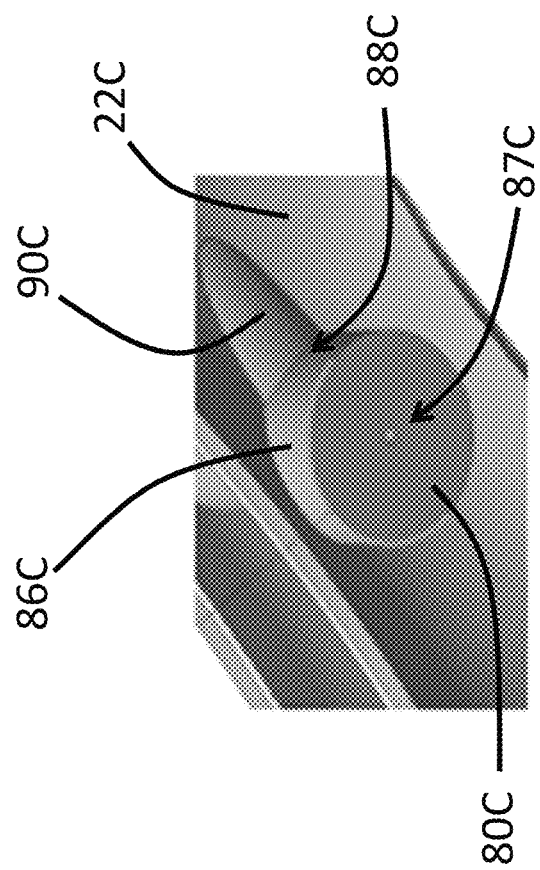
FIG. 8C is a bottom view of a portion of the fixation device of FIG. 8A.

FIG. 8C shows a bottom view of the distal plate 22C depicted in FIG. 8B. In the illustrated embodiment, the distal-facing surface of the distal plate 22C has a raised feature 90C that fits into the interlock 88C that is on the collar 86C of the pin 80C. When the raised feature 90C of the distal plate 22C is seated in the interlock 88C, rotation of the locking pin 80C about the longitudinal axis of the central guidewire 82C causes the distal plate 22C to rotate with the locking pin 80C about the longitudinal axis of the central guidewire 82C. In this way, the position of the distal plate 22C can be adjusted by manipulating the central guidewire 82C. FIG. 8D shows a bottom view of the distal plate 22C alone, i.e., without the locking pin 80C.

FIG. 9A depicts an embodiment of a device 20D that is similar in some respects to the device 20C. The features of the device 20C can be combined or included with the device 20D. The device 20D can comprise a heart valve prosthesis. The device 20D has a locking pin 80D that passes through a central opening in each of the distal and proximal plates 22D, 24D. In the illustrated embodiment, the distal plate 22D includes an eyelet 92D disposed on either end of the distal plate 22D. The eyelet 92D is adapted to receive a barb 94D that is disposed on the proximal plate 24D. The barb 94D can be configured to pierce through a valve leaflet that is secured between the distal and proximal plates 22D, 24D. The barb 94D can have wing portions 96D that spring outward as the barb 94D is pushed through the eyelet 92D. In some embodiments, the wing portions 96D are configured to prevent the barb 94D from moving proximally back through the eyelet 92D after the wing portion 96D has passed distally through the eyelet 92D. In this way, the barb 94D and eyelet 92D can lock together the distal and proximal plates 22D, 24D. While not shown in FIG. 9A, the locking pin 80D can have a distal collar 86D that is similar to the distal collar 86D shown in FIG. 8C. As discussed above, the distal collar 86D can be configured to rotate the distal plate 22D and can be configured to pull the distal plate 22D toward the proximal plate 24D when tension is applied to the central guidewire 82D.

The proximal plate 24D can be configured to have a flat configuration, as shown in FIG. 9B. In some embodiments, the proximal plate 24D is made of a shape memory material (e.g., nitinol sheet). In some embodiments, the proximal plate 24D can fold flat for delivery. In some configurations, the proximal plate 24D bends from a flat configuration (shown in FIG. 9B) to the bent configuration (shown in FIG. 9A) upon the proximal plate 22D contacting a body fluid, or being released from a restrictive sheath, or increasing in temperature.

Figure 10B:
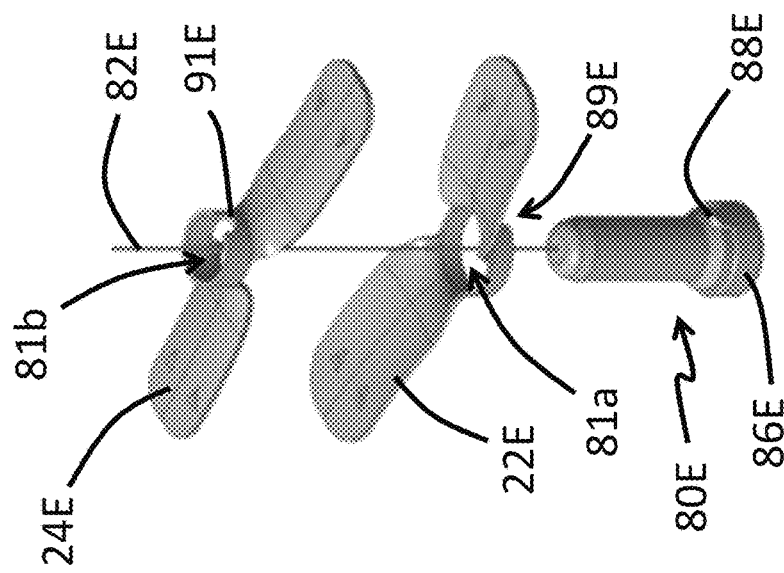
FIG. 10B is an exploded view of the fixation device of FIG. 10A.
Figure 10A:
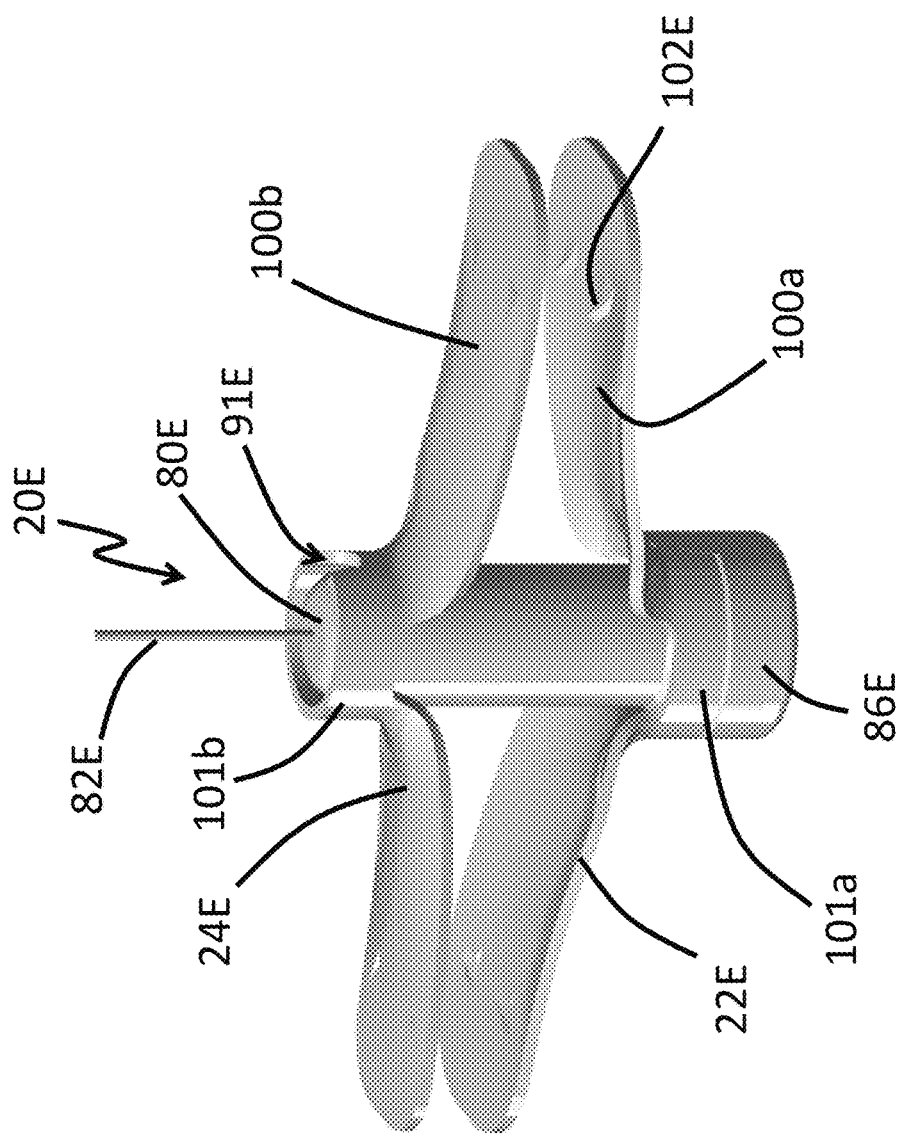
FIG. 10A is an isometric view of an embodiment of a fixation device.

FIG. 10A depicts an embodiment of a device 20E that is similar to the devices 20, 20C, and 20D except as described differently below. The features of the device 20E can be combined or included with the devices 20, 20C, and 20D or any other embodiment discussed herein. The device 20E can comprise a heart valve prosthesis. The device 20E has a locking pin 80E that passes through a central opening in each of the distal and proximal plates 22E, 24E. The distal and proximal plates 22E, 24E have wings 100a, 100b that extend laterally away from a central ring 101a, 101b. The central rings 101a, 101b are examples of tubular bodies that are disposed generally in a central portion of the distal and proximal plates 22E, 24E respectively. The wings 100a, 100b can be configured to fold into a cylinder for deliver within a sheath of a delivery catheter. When the distal and proximal plates 22E, 24E are released from the sheath of the delivery catheter, the wings 100a, 100b can spring open so that the lateral portions of the wings 100a, 100b are further from the central guidewire 82E. In FIG. 10A, the wings 100a, 100b are shown in the open or deployed configuration. As described above, the distal and proximal plates 22E, 24E can include an elastic or shape memory material that facilitates the distal and proximal plates 22E, 24E springing into the open configuration upon release of the distal and proximal plates 22E, 24E from a restricted state such as containment within a delivery sheath. In some embodiments, the distal and proximal plates 22E, 24E are fabricated from cut and formed nitinol tube. In some configurations, the distal and proximal plates 22E, 24E are shaped to allow for easy retrieval of the plate back into the delivery sheath if the procedure is aborted. For example, the proximal plate 24E can be recovered into the delivery sheath from the deployed configuration by advancing the delivery sheath distally over the proximal plate 24E to fold the wings 100b toward the central guidewire 82E. The distal plate 24E can be recovered into the delivery catheter by a lasso-like snare or by applying tension to a delivery suture that is temporary wrapped around the lateral portions of the wings 100a, thereby drawing the wings 100a toward the central guidewire 82E. In some configurations, the wings 100a, 100b have a spring-like quality that allows the wings 100a, 100b to fold toward the longitudinal axis of the central guidewire 82E while the plates 22E, 24E are being withdrawn in the proximal direction.

The distal and proximal plates 22E, 24E can include a grip feature 102E that helps secure the tissue (e.g., valve leaflet) between the distal and proximal plates 22E, 24E. In the illustrated embodiment, the grip feature 102E is a directional barb that points toward the central guidewire 82E and toward the opposing plate. The illustrated grip feature 102E facilitates "one-way" gripping of the leaflets, allowing the leaflets to only work themselves closer together with movement while preventing the leaflets from moving farther apart.

FIG. 10B is an exploded view of the device 20E depicted in FIG. 10A. The locking pin 80E can have an interlock 88E that mates with a corresponding feature on the distal plate 22E, as described above. In the illustrated embodiment, the corresponding feature is a distal notch 89E disposed on the central ring 101a of the distal plate 22E. In FIG. 10B, the distal notch 89E is partially obscured by the wing 100a of the distal plate 22E. However, the distal notch 89E is similar to the proximal notch 91E (shown in FIG. 10A) that is disposed on the central ring 101b of the proximal plate 24E. As described for some of the embodiments previously described, tension applied to the central guidewire 82E can draw the locking pin 80E through the central rings 101a, 101b of the distal and proximal plates 22E, 24E. The interlock 88E on the collar 86E of the locking pin 80E can mate with the distal notch 89E to help rotate and position the distal plate 22E. The collar 86E can be sized so that the collar 86E cannot pass through the central ring 101a of the distal plate 22E in the proximal direction. Accordingly, tension applied to the central guidewire 82E will pull the distal plate 22E in the proximal direction. A pusher tube (not shown) can be advanced distally over the central guidewire 82E and can be used to push the proximal plate 24E toward the distal plate 22E. The pusher tube can include an interlock that mates with the proximal notch 91E to allow the pusher tube to rotate and position the proximal plate 24E. In some configurations, the distal and proximal plates 22E, 24E are compressed together by pulling the distal plate 22E toward the proximal plate 24E while simultaneously pushing the proximal plate 24E toward the distal plate 22E. In some embodiments, the proximal notch 91E can receive an interference-fit locking nut 93 (shown in FIG. 19) that secures the proximal plate 24E to the locking pin 80E, as described in more detail below. The locking nut 93 is one example of a locking device. More generally in various embodiments a locking device can be provided that can provide a releasable coupling between the components of the device 20F can be employed.

Figure 11C:
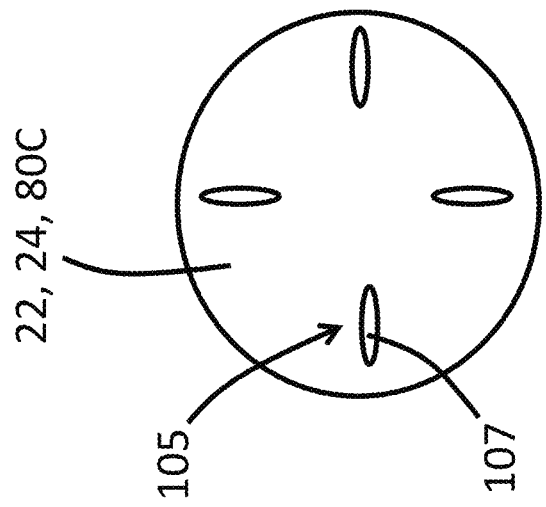
FIG. 11C is a top view of a portion of a plate or pin that has an attachment feature.
Figure 11A:
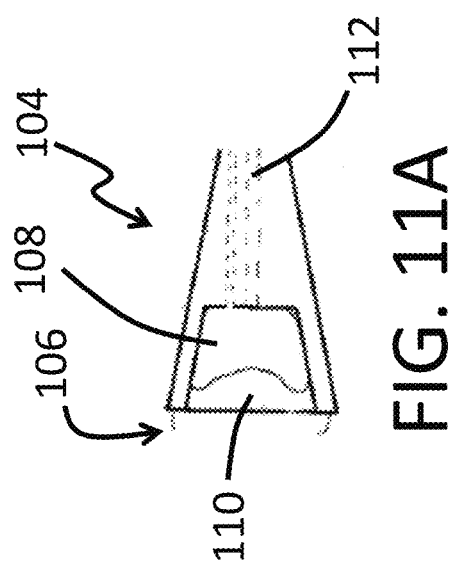
FIG. 11A is a side view of a guidewire detachment feature in the uninflated state.
Figure 11B:
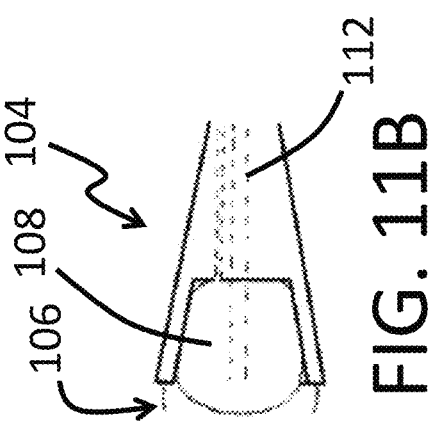
FIG. 11B is a side view of the guidewire detachment feature of 11A in the inflated state.

FIGS. 11A-C show illustrative attachment features that can allow a guidewire to be detached from the distal or proximal plates 22, 24. In the illustrated embodiment, the distal end of the attachment feature 104 can have an anchor feature 106 that mates with a receiving feature 105 (shown in FIG. 11C) disposed on a portion of the distal plate 22-22F, on a portion of the proximal plate 24-24F, or on a portion of the locking pin 80C-F. In some configurations, the anchor feature 106 can be a flexible wire that fits into a slot 107 on the distal or proximal plate 22, 24. The flexible wire can be biased radially outward with sufficient force such that when the flexible wire is inserted into the slotted receiving region the flexible wire cannot be pulled out of the slot without applying a sufficiently high threshold level of force. The threshold level of force needed to pull the anchor feature 106 from the receiving region can be selected so that it is greater than the expected force that will be applied during delivery of the distal or proximal plate.

The attachment feature 104 can have an inflatable member 108 disposed within a cavity 110 at the distal end of the attachment feature 104. The inflatable member 108 can be in fluid communication with an inflation lumen 112 that is disposed within the guidewire. FIG. 11A shows the inflatable member 108 in the deflated state, in which the inflatable member is contained within the cavity 110. The inflatable member 108 can be inflated by delivering an inflation fluid into the inflatable member 108 through the inflation lumen 112. As shown in FIG. 11B, when the inflatable member 108 is inflated, a portion of the inflatable member will extend beyond the cavity 110 and pry the anchor feature 106 from the distal or proximal plate 22, 24 (not shown), thereby disconnecting the guidewire from the distal or proximal plate 22, 24.

FIGS. 12A-C show another embodiment of the attachment feature 104A. The attachment feature 104A can include an inner elongate member 109 disposed within an outer member 111. For example, the inner and outer elongate members 109, 111 can be coaxial guidewires. The proximal ends of the inner and outer elongate members 109, 111 can include a pin or other feature that locks the inner and outer elongate members 109, 111, thereby preventing the inner and outer elongate member 109, 111 from moving relative to one another. The attachment feature 104A can include a locking element 113 that secures the inner and outer elongate members 109, 111 to the distal or proximal plate 22, 24. In the illustrated embodiment, the locking element is a ball 115 that passes through a hole of the outer elongate member 111 and sits within a recess 117 in the proximal plate 22. As shown in FIG. 12A, the end portion of the inner member 109 is tiered. In the locked position, the end portion of the inner elongate member 109 holds the ball a first distance D1 from the proximal plate 22.

To detach the attachment feature 104A from the proximal plate 22, the inner and outer elongate members 109, 111 are first unlocked (e.g., removing a locking pin that passes through the proximal ends of the inner and outer elongate members 109, 111) to allow the inner and outer elongate members 109, 111 to move relative to one another. The inner elongate member 109 is retracted proximally relative to the outer elongate member 111, as shown in FIG. 12B. This allows the ball 115 to drop out of the recess 117 so that the ball 115 is now a distance D2 away from the proximal plate 22. With the ball 115 a distance D2 away from the proximal plate 22, the outer elongate member 111 can now be withdrawn from the proximal plate 22, as shown in FIG. 12C. In this way, the attachment feature 104A can allow the inner and outer elongate members 109, 111 to be detached from the proximal plate 22.

Figure 13A:
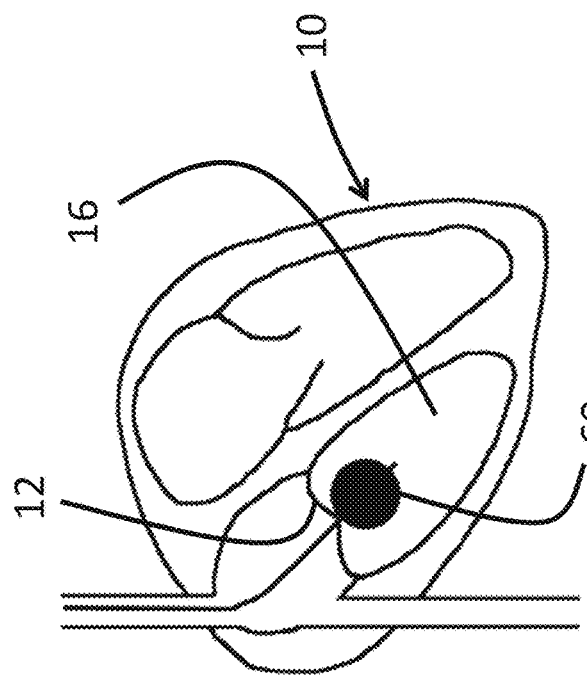
FIG. 13A is a cross-sectional view of a heart with an embodiment of an expandable fixation device. The expandable fixation device is in its unexpanded state and the heart is in diastole.
Figure 13B:
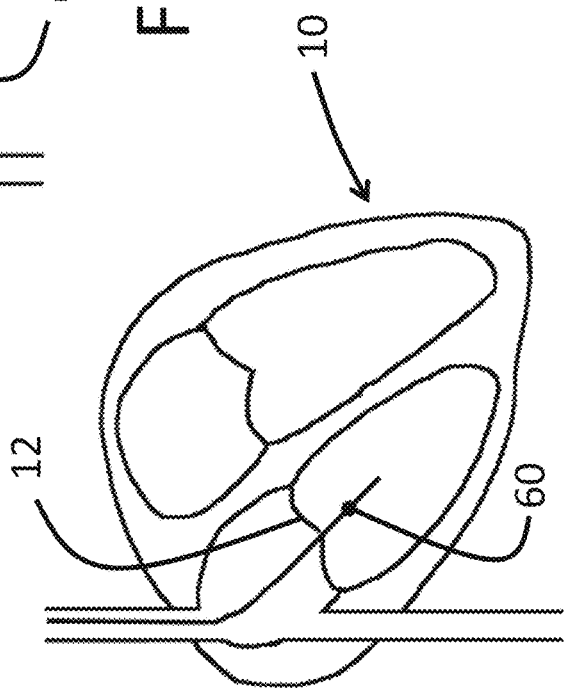
FIG. 13B depicts the embodiment of FIG. 6A with the heart in systole.
Figure 13C:
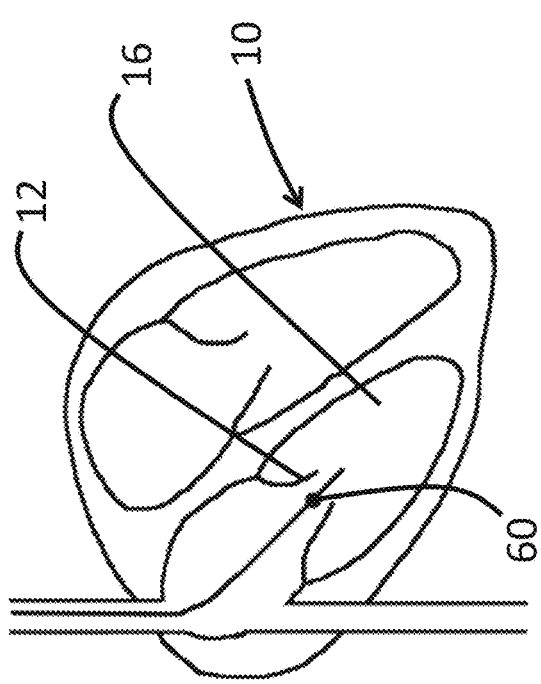
FIG. 13C is the embodiment of FIG. 6A with the expandable fixation device in its expanded configuration.

FIGS. 13A-C depict another embodiment of the present disclosure that includes the use of a collapsible and expandable feature 60 such as a balloon or wire frame that can be passed to the ventricular side of the right ventricle in the collapsed state. FIG. 13A depicts the expandable feature 60, in its unexpanded state, being advanced through superior vena cava, past the tricuspid valve 12, and into the right ventricle 16 of a heart 10 in normal diastole. FIG. 13B depicts the expandable feature 60 in its unexpanded state within the right ventricle of a heart in systole. FIG. 13C depicts the expandable feature 60 and expanded once in the right ventricle 16. The dimensions of this expandable feature 60 can be such that the expandable feature 60 can snag or catch the leaflet edges when the tricuspid valve 12 is open but not pass between them. The tension of withdrawing the expanded expandable feature 60 from the right ventricle 12 into the right atrium 14 therefore catches the leaflets of the tricuspid valve 12, forcing the leaflets closer together or into the closed position, thereby stabilizing them for fixation. In this way, the valve leaflets can be temporarily secured together. This device would allow the operator to pull back on the balloon in systole, and tent or force the leaflets into the closed position. The purpose of this is to evaluate any reduction in tricuspid regurgitation by fixing any coaptation line, or for temporarily holding two leaflets together while a permanent fixation device is affixed, as described below.

The present disclosure includes the use of a guidance rail to attain proper positioning within the tricuspid valve. In some aspects, a catheter or wire is threaded through the right atrium, through the tricuspid valve, through the right ventricle, into the right ventricular outflow tract, and into the main pulmonary artery. This catheter or wire may be guided into position utilizing flow-directed guidance, echocardiography, ultrasonography, fluoroscopy, a steerable catheter, or some combination thereof. A fixation device for the tricuspid valve can then be threaded over this guidance rail and to the level of the tricuspid valve.

Figure 14:
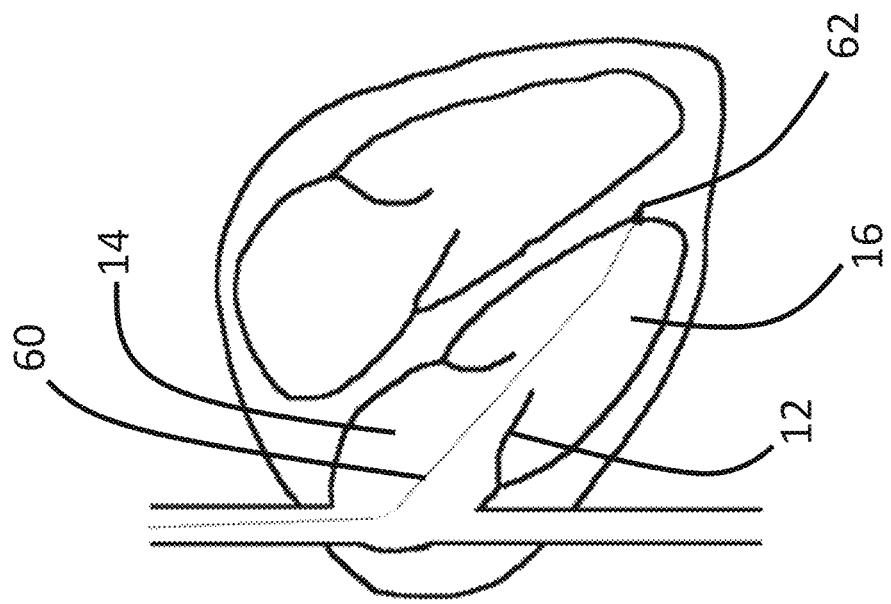
FIG. 14 is an embodiment of a fixation device having a guidance rail embedded into the ventricular wall.

FIG. 14 depicts another embodiment of the present disclosure that includes the use of a guidance rail. The guidance rail 60 can be advanced through the right atrium 14, past the tricuspid valve 12, and embedded into the right ventricle 16. In some aspects, a catheter or wire with a penetrating threaded tip 62 can be advanced via a delivery catheter into the right ventricle. The threaded tip 62 may be configured to bore into the interventricular septum or some other portion of the right ventricle such that the catheter or wire can be made taut under tension. Positioning and guidance can be provided utilizing echocardiography, ultrasonography, fluoroscopy, or some combination. The delivery catheter can then be removed. A fixation device for the tricuspid valve 12 can then be threaded over the guidance rail 60 and to the level of the tricuspid valve 12. At the conclusion of the procedure, the guidance rail 60 can be removed either in its entirety, or leaving the penetrating threaded tip 62 in situ and removing only the catheter or wire portion.

Figure 15:
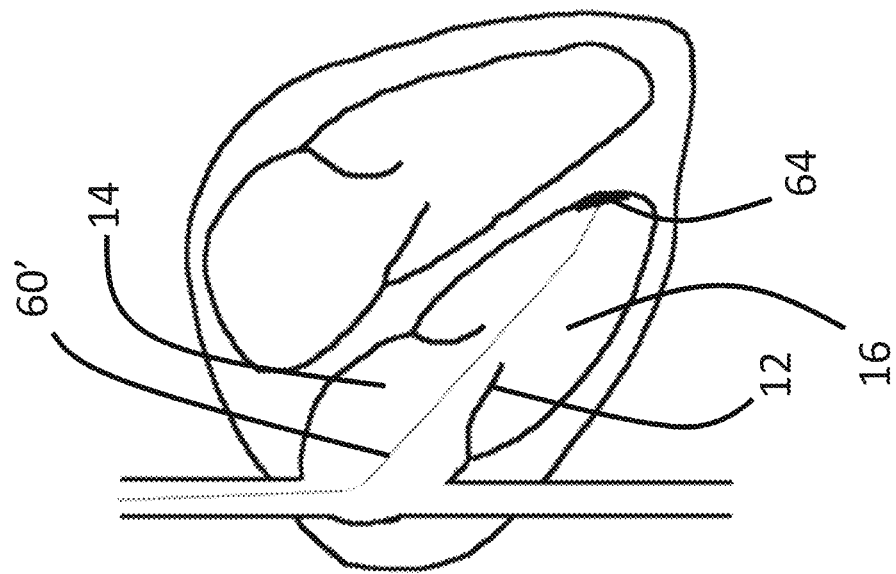
FIG. 15 is an embodiment of a fixation device having a suction tip.

FIG. 15 depicts another embodiment of the present disclosure that includes the use of a guidance rail. A removable guidance rail 60' may be advanced through the right atrium 14, past the tricuspid valve 12, and secured against a wall of the right ventricle 16. The removable guidance rail 60' may be secured using suction. A catheter or wire with a deployable, high compliance, and large area suction tip 64 can be advanced into the right ventricle 16 via a delivery catheter. The suction tip 64 can be positioned against a ventricular wall surface and suction can be applied, holding the suction tip 64 firmly against some portion of the right ventricle 16 such that the catheter or wire can be made taut under tension. Positioning and guidance can be provided utilizing echocardiography, ultrasonography, fluoroscopy, or some combination. The delivery catheter can then be removed. A fixation device for the tricuspid valve 12 can then be threaded over this guidance rail 60' and delivered to the level of the tricuspid valve 12.

Figure 16:
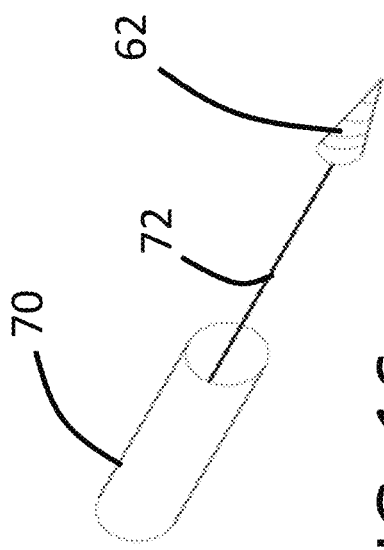
FIG. 16 is an embodiment of a threaded tip for embedding into the ventricular wall.

FIG. 16 depicts an embodiment of the present disclosure that includes a threaded tip 62. A delivery catheter 70 may be used to guide and deliver the threaded tip 62 into the right ventricle. The threaded tip 62 can have a penetrating tip. Torque can be transmitted through the delivery catheter 70 or through a wire 72 connected to the threaded tip 62.

Figure 17B:
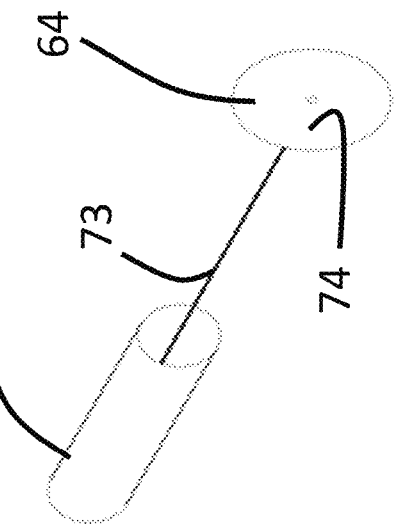
FIG. 17B is an isometric view of the embodiment of FIG. 10A in its fully deployed configuration.
Figure 17A:
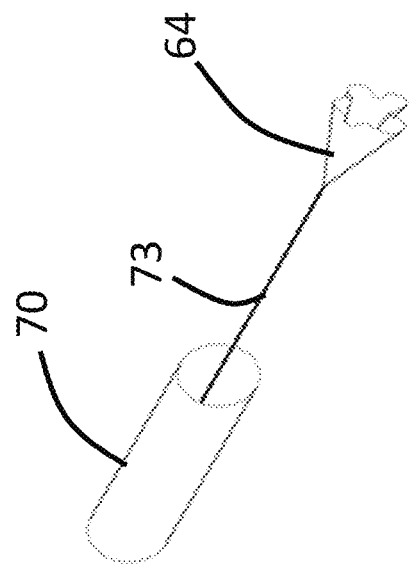
FIG. 17A is an isometric view of an embodiment of a suction tip in its partially deployed configuration.

FIGS. 17A and 17B depict another embodiment of the present disclosure that includes a suction tip 64. The suction tip 64 can be a high area, high compliance skirt. The suction tip 64 can be stowed within the delivery catheter 70. FIG. 17A depicts the suction tip 64 partially unfurled from its stowed configuration. FIG. 17B depicts the suction tip 64 in its fully deployed configuration. When unfurled, the suction tip can form a skirt that can be applied to a ventricular surface. Suction can be applied to secure the suction tip 64 to the ventricular wall. The suction tip 64 may be coupled to a guidewire 73. The guidewire 73 may contain a lumen that allows suction to be applied to the distal face 74 of the suction tip 64. Suction can be provided by external aspiration.

Figure 18:
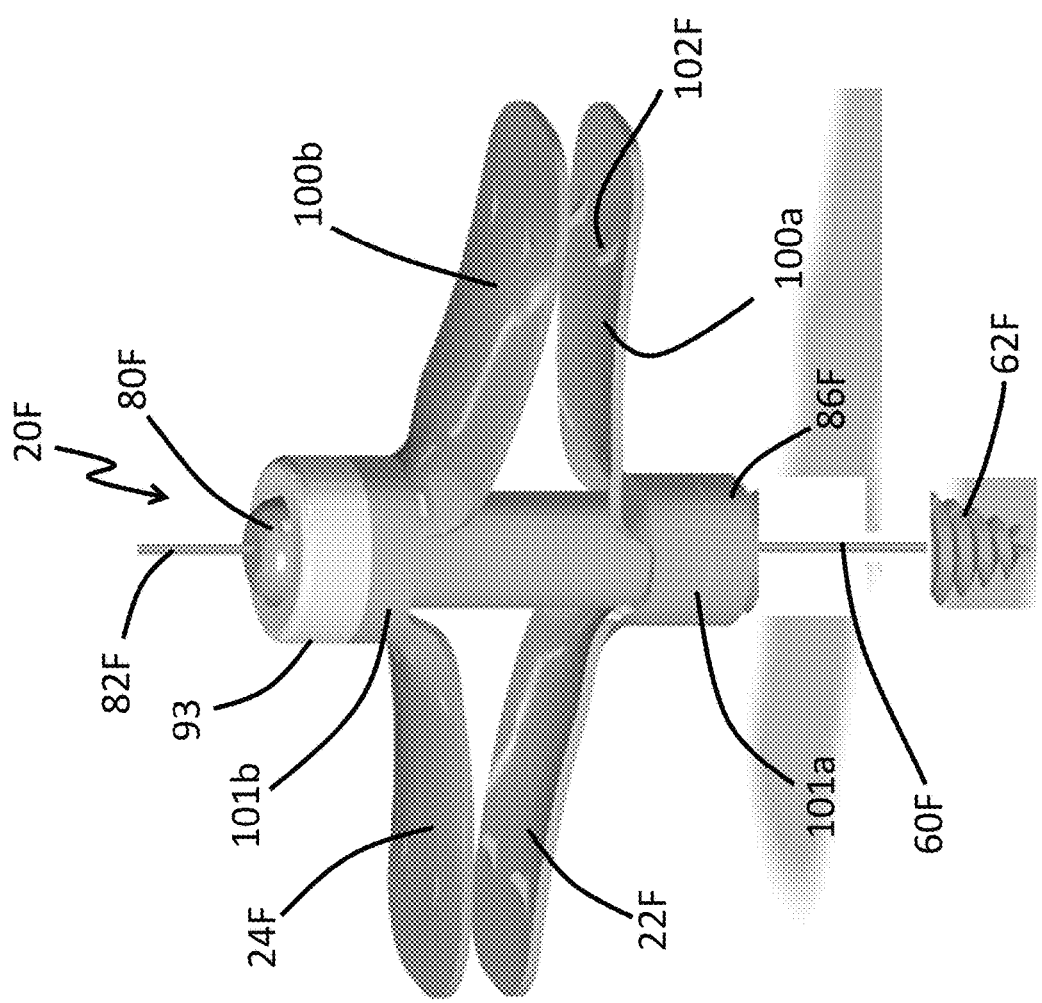
FIG. 18 is an isometric view of an embodiment of a fixation device deployed over a guidance rail.

FIG. 18 depicts an embodiment of a device 20F that is similar to the devices 20 and 20C-20E except as described differently below. The features of the device 20F can be combined or included with the devices 20 and 20C-20E or any other embodiment discussed herein. The device 20F can comprise a heart valve prosthesis. The device 20F has a locking pin 80F and configured to be deployed over a guidance rail 60F. The central guidewire 82F can be hollow and can concentrically surround the guidance rail 60F that is connected to the threaded tip 62F. The locking pin 80F can be connected to the central guidewire 82F using a detachable attachment feature 104 described above. The distal face of the locking pin 80F can have an opening 87F (shown in FIG. 8C) that provides access to a rail lumen (not shown) of the hollow central guidewire 82F. The device 20F can be preassembled by passing the proximal end of the rail 60F through the opening 87F and into the rail lumen of the hollow central guidewire 82F. The rail 60F can be sufficiently sized to pass out the proximal end of the hollow central guidewire 82F. The hollow central guidewire 82F may also include an inflation lumen for detaching the detachable attachment feature 104, as described above.

To deploy the device 20F, the guidance rail 60F can first be advanced and anchored in the right ventricle. The locking pin 80F and hollow central guidewire 82F that were preassembled onto the guidance rail 60F can then be advanced along the anchored rail 60F. The distal plate 22F can then be advanced over the hollow central guidewire 82F and positioned using the collar 86F on the locking pin 80F. The proximal plate 24F can then be advanced over the central guidewire 82F. A pusher tube inserted over the central guidewire 82F can be used to advance and position the proximal plate 24F, as described above. The distal and proximal plates 22F, 24F can then be secured together by the locking pin 80F. The central guidewire 82F can then be detached from the distal and proximal plates 22F, 24F by inflating the member 106 of the detachable attachment feature 104.

FIG. 19 depicts a top view of a tricuspid valve 12, illustrating that the present disclosure envisions variable placement of the device 20 or any of the other devices 20A-20F, as denoted by the dashed lines indicating potential locations L of the device 20. Positioning of the device 20-20F is variable depending on the location of tricuspid regurgitation. For the majority of cases, an attempt may be made to "bicuspidize" the tricuspid valve by deploying one or more devices 20-20F along any single coaptation line, such that two leaflets are now attached and function as a single large leaflet. In some methods, echocardiography and fluoroscopy are used in conjunction with a steerable tip delivery catheter to achieve device positioning that best limits regurgitation. A device can then be deployed at that location and valve regurgitation can be re-evaluated. If needed, additional devices may be deployed to further reduce valve regurgitation.

FIGS. 19A-19G illustrate a variety of delivery systems and methods that can be combined with the devices 20-20F. The delivery systems can be employed in methods to place the devices 20-20F as discussed above.

Figure 19A:
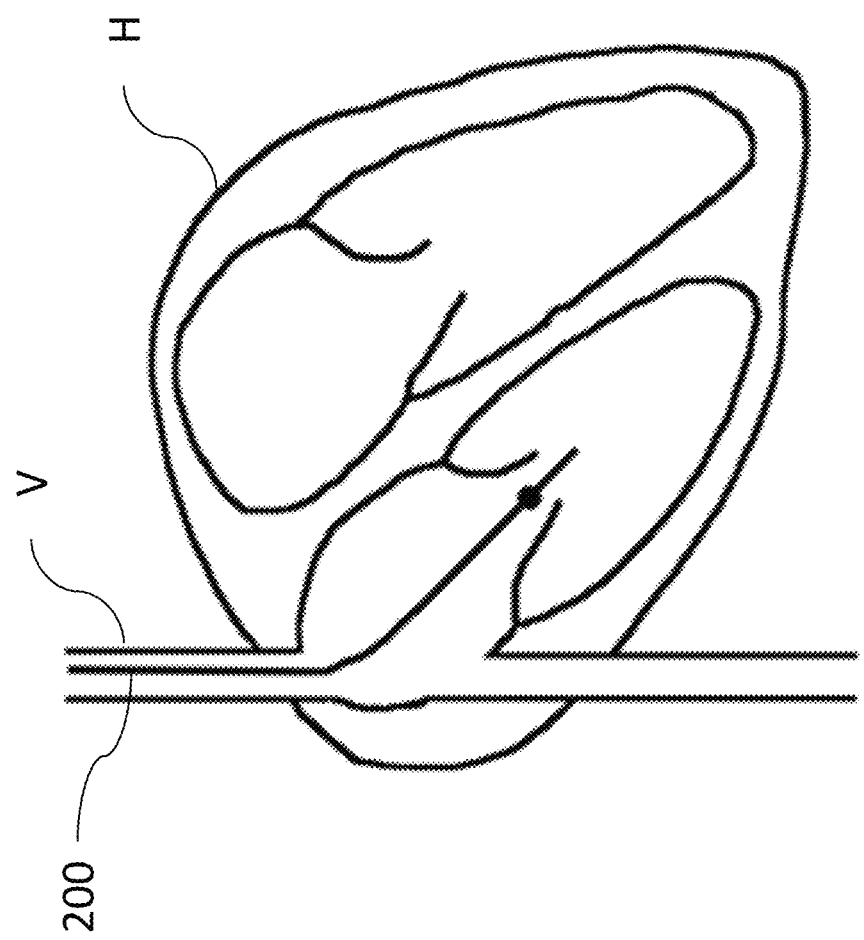
FIG. 19A is a cross-sectional view of a heart showing placing a guidewire along the venous vasculature into the heart.
Figure 19B:
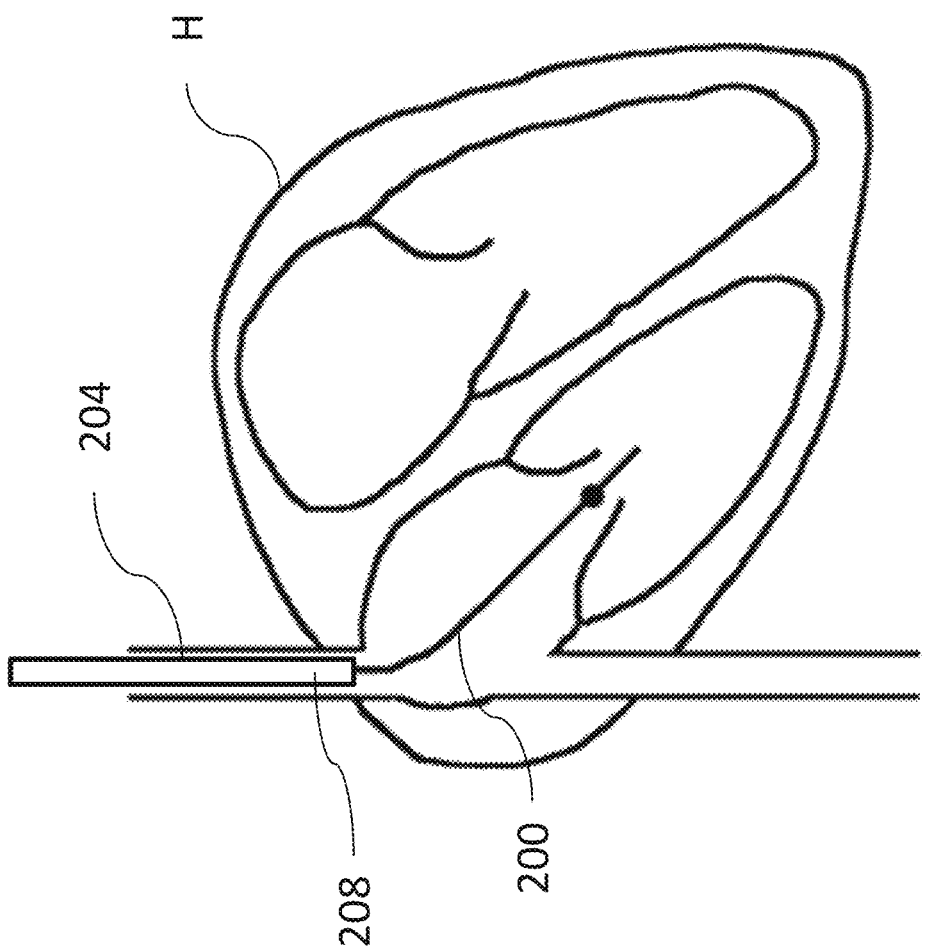
FIG. 19B is a cross-sectional view of a heart showing advancing a delivery system along a guidewire into the heart.
Figure 19C:
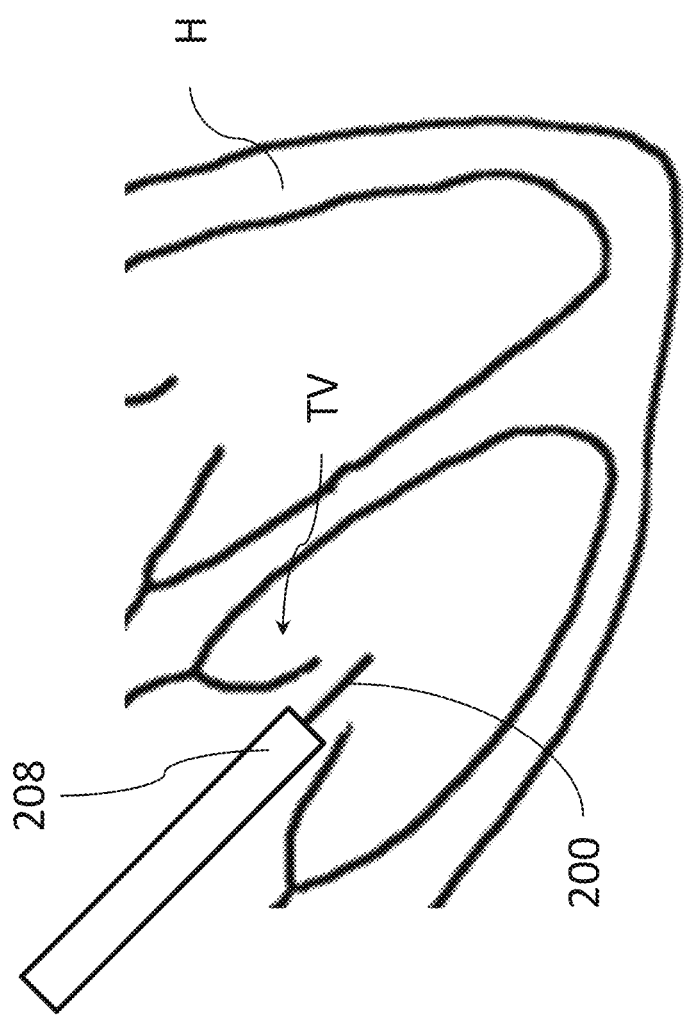
FIG. 19C is a cross-sectional view of a heart showing a delivery system in the vicinity of a heart valve.
Figures 1, 19C:
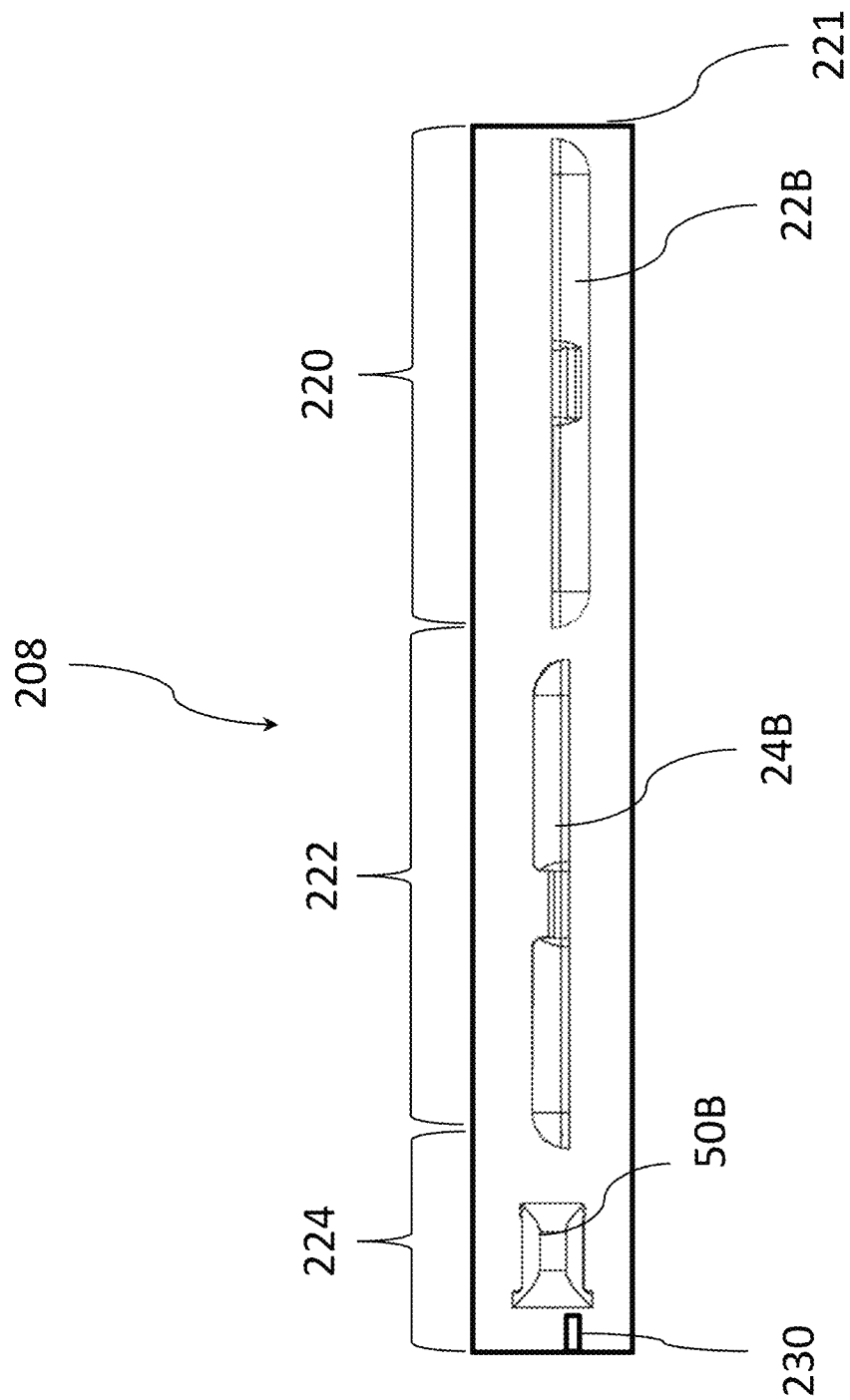
Figures 2, 19C:
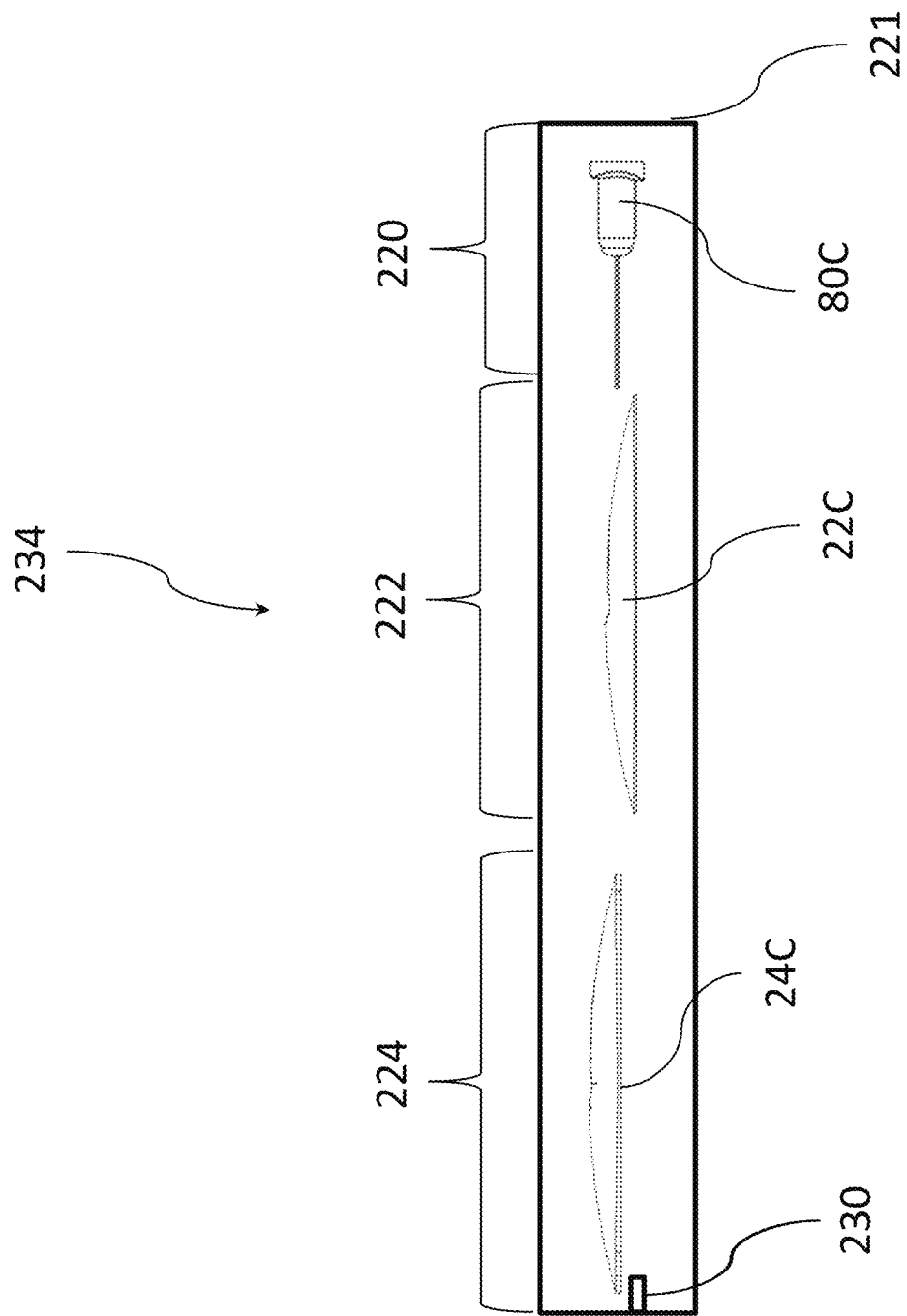

FIG. 19A shows placing a guidewire 200 along the venous vasculature V into the heart H. The guidewire 200 can be a flow directed guidewire or can be delivered using other techniques. FIG. 19B shows that a delivery system 204 is advanced over the guidewire 200 until a distal portion 208 of the delivery system 204 is disposed adjacent to the heart H. The proximal portion of the delivery system 204 is not shown but would be outside the patient at a peripheral access site. As discussed further below, the delivery system 204 includes a catheter that is configured to deliver some or all of the components of any of the devices 20-20F therein in an unassembled state. In other approaches, separate catheters can be used to deliver individual components of the device 20-20F.

FIG. 19C shows that further advancement of the delivery system 204 places the distal end 208 in the heart H, in particular at or across the tricuspid valve TV. Thereafter, the components of the device 20-20F can be deployed individually.

FIG. 19C-1 shows details of the internal arrangement within the distal end 208 of the delivery system 204. For example, the device 20B is disposed in the distal end 208 in an unassembled state. The distal plate 22B, which is one form of a distal member or a first member, is disposed in a first segment 220 of the distal portion 208. The first segment 220 can be a distal-most segment that extends from a distal tip 221 of the distal portion 208 proximally to a location proximal of the distal plate 22B. The proximal plate 24B, which is one form of a proximal member or a second member, is disposed in a second segment 222 of the distal portion 208. The second segment 222 is disposed immediately proximal of the first segment 220. In this way, the proximal plate 24B is disposed between the distal plate 22B and a proximal end of the delivery system 204. The distal plate 22B and the proximal plate 24B are aligned end-to-end in the distal end 208 of the delivery catheter 204. Ends of the plates 22B, 24B that oppose each other are spaced apart along the length of the distal portion 208. The locking clip 50B is an example of a connector that connects the plates 22B, 24B by being advanced from a proximal side of the proximal plate 24B over the proximal plate 24B, then over a proximal side of the distal plate 22B until it engages the distal plate 22B as discussed above. The locking clip 50B is disposed in a third segment 224 of the distal portion 208 that is disposed immediately proximal of the second segment 222.

A pusher member 230, which can be a pusher catheter, can be disposed in a lumen of the delivery catheter 204. The pusher member 230 can act on any one or more of the distal plate 22B, 24B, or clip 50B to move these components out of the delivery catheter 204 into the heart.

FIG. 19C-2 shows another embodiment of a delivery system 234 that can be similar to the system 204 except as described differently below. The delivery system 234 has first, second and third segments 220, 222, 224. The locking pin 80C, which is another form of a connector as disclosed herein, can be disposed in the first segment 220. The locking pin 80C is an example of a connector as disclosed herein that is advanced into the heart first and thereafter is a base onto which distal and proximal plates 22C, 24C are mounted. In the system 234, the distal plate 22C is disposed in the second segment 222 and the proximal plate 24C is disposed in the third segment 224. A fourth segment can include a space configured to house a locking nut or other locking device that can be used to secure the distal and proximal plates 22C, 24C.

Figure 19D:
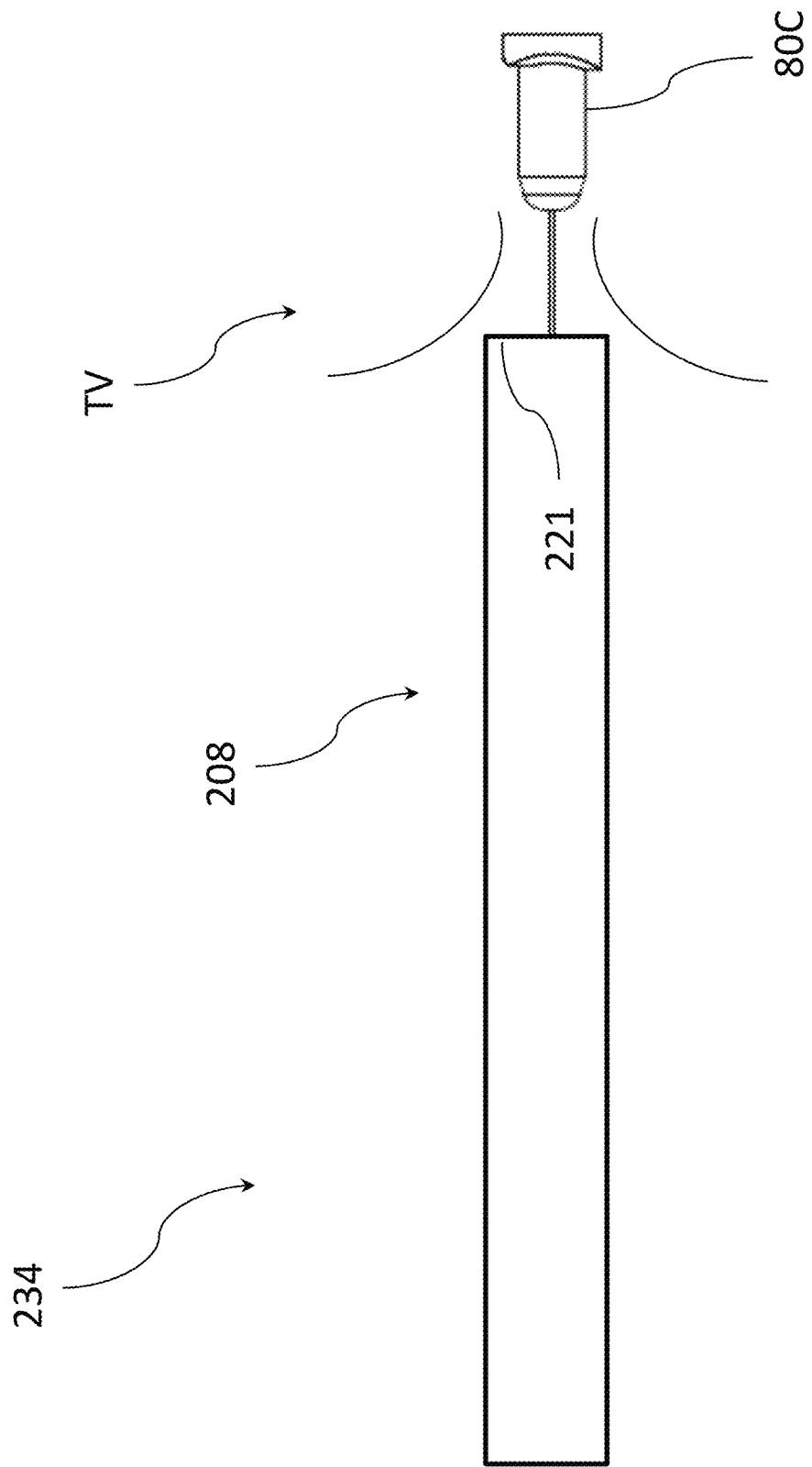
FIG. 19D shows a pin being deployed from a delivery device.
Figure 19E:
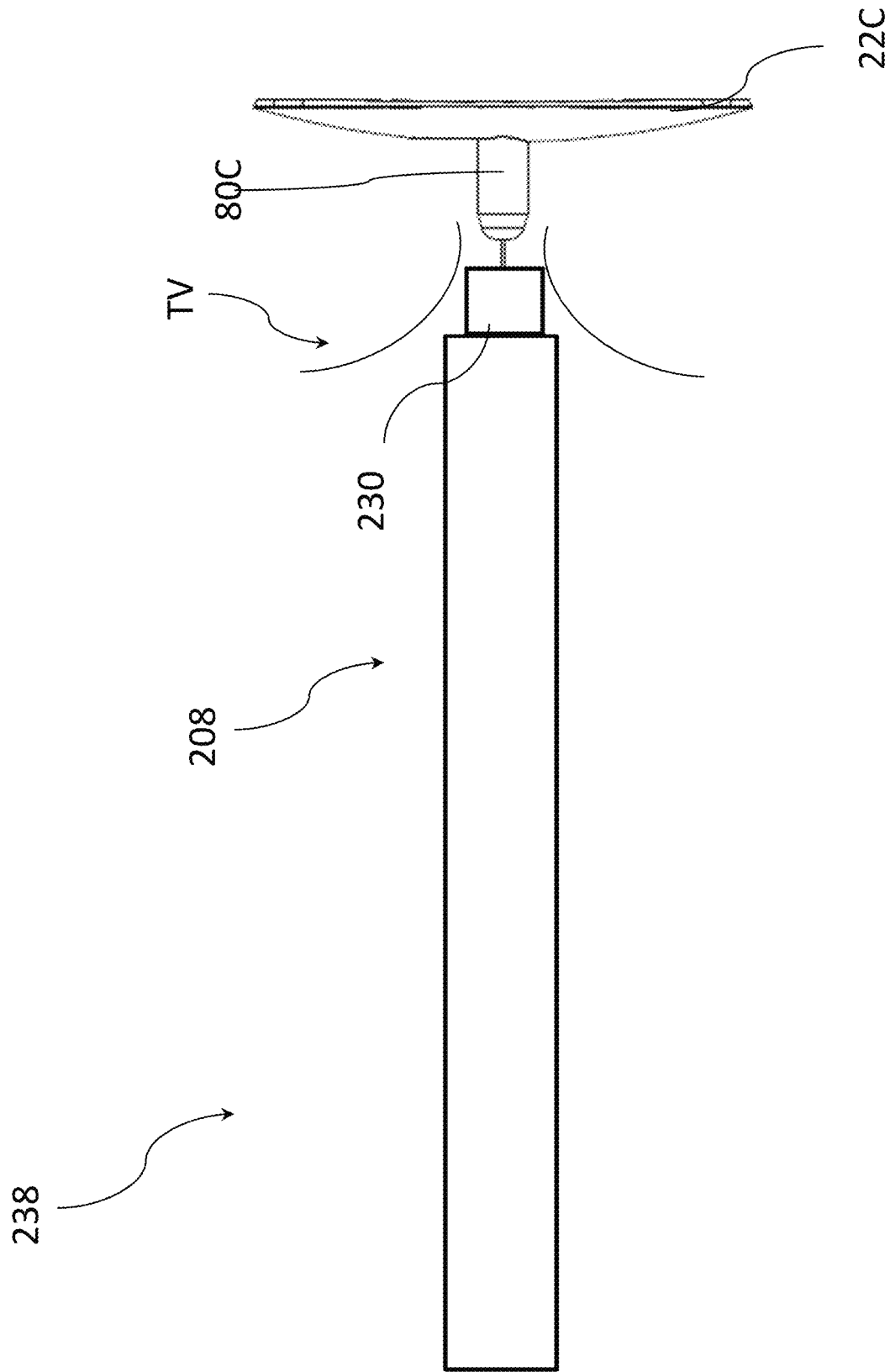
FIG. 19E shows a distal plate being deployed from a delivery device.
Figure 19F:
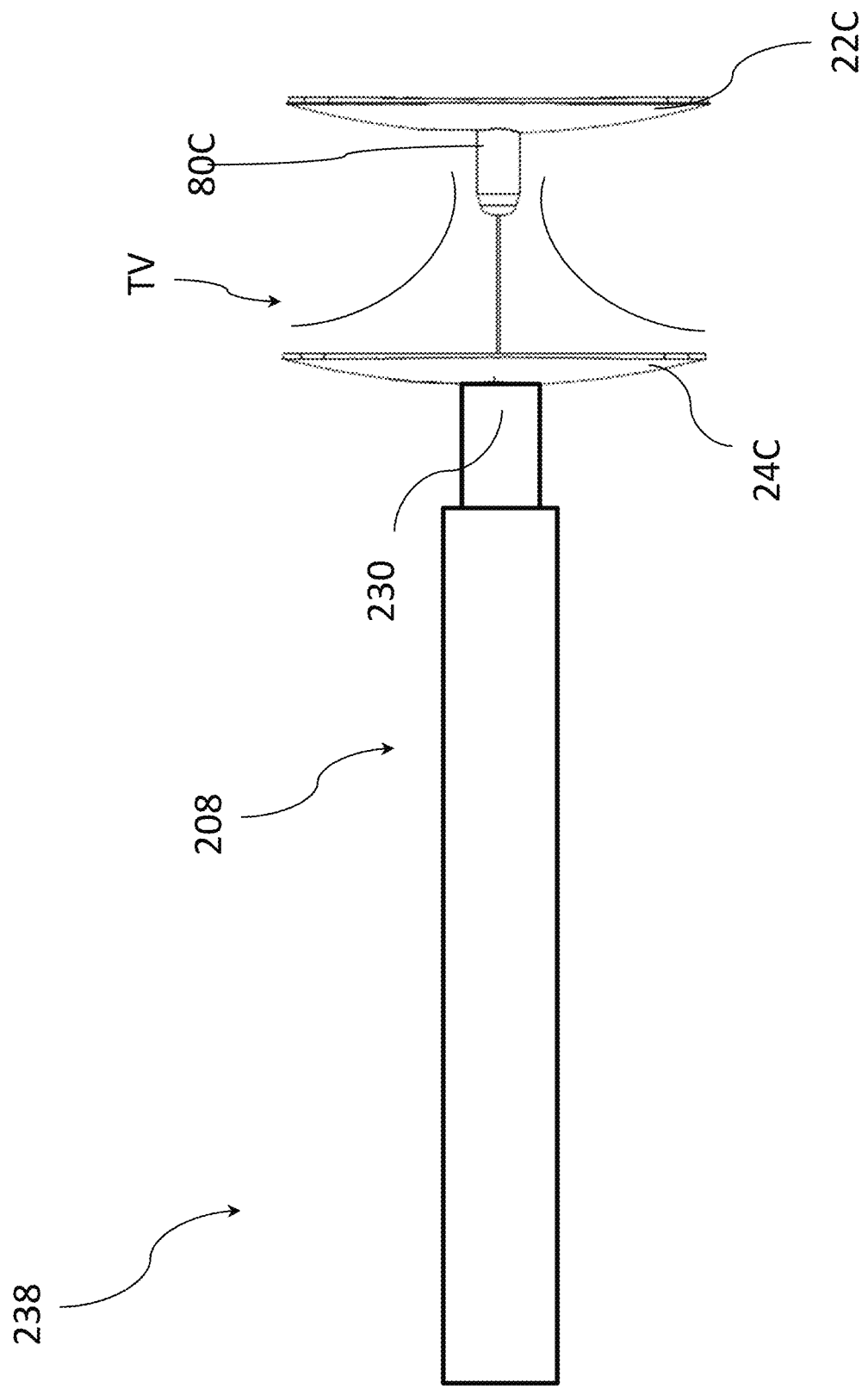
FIG. 19F shows a proximal plate being deployed from a delivery device.

FIGS. 19D-19G illustrate the use of the delivery system 234 to build the device 20C within the heart. The locking pin 80C, which is a form of a connector, is advanced out of the distal tip 221 of the distal portion 208. FIG. 19D show that the locking pin 80C can be advanced across leaflets of the valve TV. Such movement can be by floating the pin 80C or by pushing it using the pusher member 230. Such movement can result from holding the pin 80C stationary in the right ventricle and withdrawing the distal tip 221. FIG. 19E shows that thereafter the distal plate 22C can be advanced over the proximal end of the locking pin 80C. The advancement of the distal plate 22C can be achieved by then pusher member 230 which can thereafter be withdrawn back into the distal portion 208.

Figure 19G:
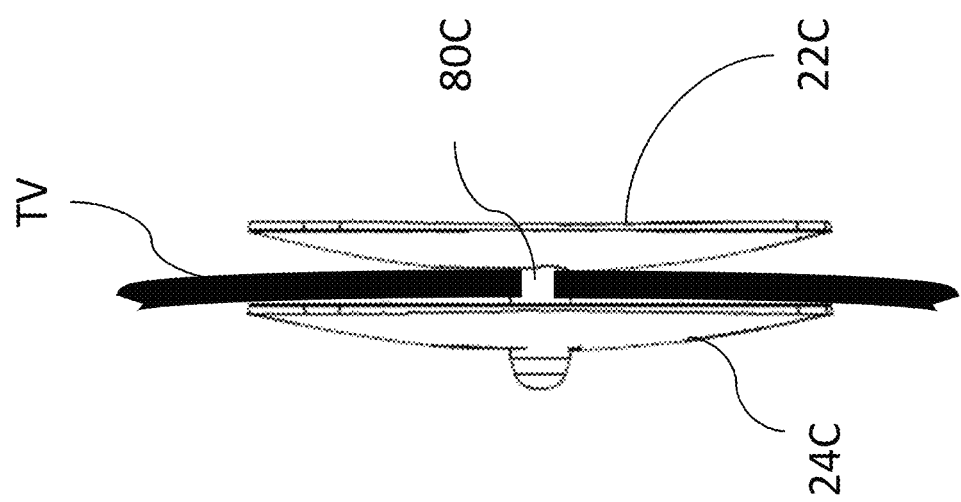
FIG. 19G shows a device deployed on a heart valve.

After the distal plate 22C is seated on the locking pin 80C, the proximal plate 24C can be advanced out of the distal portion 208, for example using the pusher member 230. As the proximal plate 24C is advanced over the pin 80C the leaflets of the tricuspid valve TV are brought together and trapped. The proximal plate 24C can be secured to the pin 80C by an interference fit between the proximal plate 24C and the pin 80C. In addition, or in the alternative, a locking nut as discussed above in connection with FIG. 18 can be advanced over the proximal portion of the locking pin 80C to removeably or releasably secure the proximal plate 24C to the locking pin 80C. FIG. 19G shows the leaflet of the tricuspid valve TV secured in a space between a proximal surface of the distal plate 22C and a distal surface of the proximal plate 24C. The leaflet thickness of the tricuspid valve TV is much greater in FIG. 19G illustrating that the space between the plates 22C, 24C can be such that the leaflets fit in the space but are securely trapped, such as by at least some compression of the leaflets.

Another aspect of the present disclosure may include the use of a grasper that relies on suction to securely hold each leaflet in position for repair. This grasper can include a series of orifices that are connected to an externally actuated source of vacuum, such that a leaflet positioned in proximity to the orifices will be sucked against the orifices, reducing leaflet movement.

Another aspect of the present disclosure may achieve fixation of the leaflet edges by securing the individual leaflet coaptation edges first, then fixing the edges of two adjacent edges together. This can be performed by any securing method such as by applying a suture or staple with or without a pledget to each leaflet coaptation edge, then securing the two sutures or staples together. This method may require the operator to secure only one leaflet edge at a time, rather than two edges simultaneously. The present methods may include affixing a winged feature to each leaflet edge individually, then securing the features together and thereby securing the leaflet edges together. The present disclosure also includes the technique of externalizing sutures that may be applied to the leaflet edges itself, or to a winged feature which is affixed to the leaflet edges, externalizing these sutures, and tying and passing the suture knot intravascularly to the tricuspid valve.

Another embodiment of this device achieves fixation by securing two adjacent leaflet edges by tension, clamp, or suction, and applying a fixation device such as a suture or staple, with or without a pledget, to the two adjacent leaflet edges, thereby securing them together.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A method of performing a procedure in a heart, comprising:
   providing a delivery catheter to a heart;
   passing a distal plate through the delivery catheter and into a right ventricle of the heart;
   drawing the distal plate against a leaflet of a tricuspid valve, wherein drawing the distal plate against the leaflet comprises applying tension to a guidewire that passes through a proximal plate;
   passing the proximal plate through the delivery catheter and into a right atrium of the heart;
   positioning the distal and proximal plates such that the leaflet of the tricuspid valve is between the distal and proximal plates; and
   securing the distal plate to the proximal plate by passing a proximal portion of a cylindrical member through a channel disposed along a longitudinal axis of the proximal plate, wherein a wall of the channel is positioned entirely proximal of a radially extending portion of the proximal plate.

2. The method of claim 1, wherein aligning further comprises the distal and proximal plates, wherein aligning comprises moving one or both of the distal and proximal plates such that a passageway is disposed across the distal and proximal plates.

3. The method of claim 2, wherein the passageway comprises a first slot or recess in the distal plate that aligns with a second slot or recess in the proximal plate.

4. The method of claim 1, wherein the distal plate is in a low-profile state during at least a portion of the passing, and wherein the distal plate is in a deployed state during at least a portion of the drawing.

5. A method of performing a procedure in a heart, comprising:
   passing a first member through a delivery catheter and into a ventricle of the heart, the first member being fixed in at least one degree of freedom to a cylindrical member disposed proximally thereof;
   passing a second member through the delivery catheter and into an atrium of the heart to allow expansion of an expandable structure of the second member, the expandable structure being coupled with and extending peripherally from a central tubular body of the second member, a portion of the central tubular body of the second member extending proximally from the expandable structure;

positioning the first and second members such that a leaflet of a heart valve is disposed therebetween;

moving a portion of the cylindrical member beyond a distal end of the expandable structure of the second member;

after moving the portion of the cylindrical member beyond the distal end of the expandable structure of the second member, moving the cylindrical member of the first member into the central tubular body of the second member; and locking the first member to the second member by positioning the cylindrical member within the central tubular body of the second member while the cylindrical member is aligned with the central tubular body of the second member.

6. The method of claim 5, further comprising connecting a first central opening of the first member and a second central opening of the second member to lock the first member to the second member.

7. The method of claim 5, wherein the first and second members are folded when within the delivery catheter.

8. The method of claim 5, wherein the first and second members expand when exiting the delivery catheter.

9. The method of claim 5, wherein the first and second members are made of an elastic or shape memory material.

10. The method of claim 5, wherein at least one of the first and second members comprise a grip feature configured to secure a tissue between the first and second members.

11. A method of performing a procedure in a heart, comprising:

passing a distal plate through a delivery catheter into a ventricle of the heart;

drawing the distal plate against a leaflet of a valve separating the ventricle from an adjacent atrium;

passing a proximal plate through the delivery catheter and into the adjacent atrium of the heart, wherein a channel disposed along a longitudinal axis of the proximal plate receives a portion of a guidewire when the proximal plate is in a low profile configuration within the delivery catheter;

positioning the distal and proximal plates such that the leaflet of the valve is between the distal and proximal plates;

advancing a proximal portion of a cylindrical member proximally of a proximal most portion of a radially extending portion of the proximal plate;

after advancing the proximal portion of the cylindrical member proximally of a proximal most portion of the radially extending portion of the proximal plate, passing the proximal portion of the cylindrical member through the channel disposed along the longitudinal axis of the proximal plate to a position within the channel proximal of the proximal most portion of the radially extending portion of the proximal plate; and securing the distal plate to the proximal plate.

12. The method of claim 11, further comprising aligning the distal and proximal plates, wherein aligning further comprises moving one or both of the distal and proximal plates such that a passageway is disposed across the distal and proximal plates.

13. The method of claim 12, wherein the passageway comprises a first slot or recess in the distal plate that aligns with a second slot or recess in the proximal plate.

14. The method of claim 11, wherein the distal plate is in a low-profile state during at least a portion of the passing, and wherein the distal plate is in a deployed state during at least a portion of the drawing.

* * * * *